(12) United States Patent
DeWitt et al.

(10) Patent No.: US 7,541,048 B2
(45) Date of Patent: Jun. 2, 2009

(54) COATING COMPOSITIONS FOR BIOACTIVE AGENTS

(75) Inventors: David M. DeWitt, Minneapolis, MN (US); Michael J. Finley, Saint Louis Park, MN (US); Laurie R. Lawin, New Brighton, MN (US)

(73) Assignee: SurModics, Inc., Eden Prairie, MN (US)

( * ) Notice: Subject to any disclaimer, the term of this patent is extended or adjusted under 35 U.S.C. 154(b) by 582 days.

(21) Appl. No.: 11/099,910

(22) Filed: Apr. 6, 2005

(65) Prior Publication Data

US 2005/0220840 A1 Oct. 6, 2005

Related U.S. Application Data

(60) Provisional application No. 60/559,821, filed on Apr. 6, 2004.

(51) Int. Cl.
*A61F 2/00* (2006.01)
*A61K 9/14* (2006.01)

(52) U.S. Cl. .................... 424/424; 424/487

(58) Field of Classification Search ............ 424/424, 424/487
See application file for complete search history.

(56) References Cited

U.S. PATENT DOCUMENTS

| | | | |
|---|---|---|---|
| 3,993,612 A | 11/1976 | Aihara et al. |
| 4,069,307 A | 1/1978 | Higuchi |
| 4,292,965 A | 10/1981 | Nash |
| 4,391,797 A | 7/1983 | Folkman |
| 4,409,206 A | 10/1983 | Stricker |
| 4,603,152 A | 7/1986 | Laurin |
| 4,623,346 A | 11/1986 | von Bittera |
| 4,627,852 A | 12/1986 | von Bittera |
| 4,693,887 A | 9/1987 | Shah |
| 4,722,906 A | 2/1988 | Guire |
| 4,768,507 A | 9/1988 | Fischell et al. |
| 4,826,759 A | 5/1989 | Guire |
| 4,867,968 A | 9/1989 | Allen |
| 4,916,193 A | 4/1990 | Tang |
| 4,959,217 A | 9/1990 | Sanders |
| 4,968,539 A | 11/1990 | Aoyagi |
| 4,973,493 A | 11/1990 | Guire |
| 4,979,959 A | 12/1990 | Guire |
| 4,994,071 A | 2/1991 | MacGregor |
| 5,002,582 A | 3/1991 | Guire |
| 5,019,096 A | 5/1991 | Fox |
| 5,114,719 A | 5/1992 | Sabel |
| 5,165,952 A | 11/1992 | Solomon |
| 5,180,366 A | 1/1993 | Woods |
| 5,217,492 A | 6/1993 | Guire |
| 5,221,698 A | 6/1993 | Amidon |
| 5,248,732 A | 9/1993 | Drzewinski ............ 525/133 |
| 5,258,041 A | 11/1993 | Guire |
| 5,263,992 A | 11/1993 | Guire |
| 5,304,121 A | 4/1994 | Sahatjian |
| 5,310,559 A | 5/1994 | Shah |
| 5,342,348 A | 8/1994 | Kaplan |
| 5,356,433 A | 10/1994 | Rowland |
| 5,380,299 A | 1/1995 | Fearnot |
| 5,414,075 A | 5/1995 | Swan |
| 5,419,760 A | 5/1995 | Narciso |
| 5,431,790 A | 7/1995 | Nesburn et al. |
| 5,437,656 A | 8/1995 | Shikani |
| 5,443,505 A | 8/1995 | Wong |
| 5,447,724 A | 9/1995 | Helmus |
| 5,449,382 A | 9/1995 | Dayton |
| 5,451,424 A | 9/1995 | Solomon |
| 5,464,650 A | 11/1995 | Berg |
| 5,466,233 A | 11/1995 | Weiner |
| 5,474,783 A | 12/1995 | Miranda et al. |
| 5,512,055 A | 4/1996 | Domb |
| 5,512,329 A | 4/1996 | Guire |
| 5,525,348 A | 6/1996 | Whitbourne |
| 5,545,208 A | 8/1996 | Wolfe |
| 5,563,056 A | 10/1996 | Swan |

(Continued)

FOREIGN PATENT DOCUMENTS

EP    0 281 482 A1    7/1988

(Continued)

OTHER PUBLICATIONS

Sasabe et al., "Dielectric Relaxations and Electrical Conductivities of Poly(alkyl Methacrylates) under High Pressure", J. Polymer science 6 (1968) pp. 1401-1418.
Computer Translation for JP-017851 previously cited, Jan. 1995 (publication date), Takao et al.
Dev, Vishva, et al., Kinetics of Drug Delivery to the Arterial Wall Via Polyurethane Coated Removable Nitinol Stent-Comparative Study of 2 Drugs, Cedars-Sinai Medical Center, Los Angeles, CA, Circulation, vol. 88, No. 4, Part 2, Oct. 1993.
Riggs, P.D. et al., "Chlorhexidine release from room temperature polymerising methacrylate systems," Biomaterials 21, 2001, pp. 345-351.
Database WPI Section Ch, Week 197837, Derwent Publications Ltd., London, GB; JP 53 090697 A (Japanese Geon Co Ltd.) Aug. 9, 1978 abstract.

(Continued)

*Primary Examiner*—Raymond J Henley, III
(74) *Attorney, Agent, or Firm*—Pauly, DeVries Smith & Deffner, L.L.C.

(57) ABSTRACT

A coating composition and related method for use in applying a bioactive agent to a surface in a manner that will permit the bioactive agent to be released from the coating in vivo. The composition is particularly well suited for coating the surface of implantable medical device, such as a stent or catheter, in order to permit the device to release bioactive agent to the surrounding tissue over time. The composition includes a plurality of compatible polymers having different properties that can permit them to be combined together to provide an optimal combination of such properties as durability, biocompatibility, and release kinetics.

46 Claims, 1 Drawing Sheet

U.S. PATENT DOCUMENTS

| | | | |
|---|---|---|---|
| 5,567,417 A | 10/1996 | Sasisekharan | 424/94.5 |
| 5,569,463 A | 10/1996 | Helmus | |
| 5,578,075 A | 11/1996 | Dayton | |
| 5,591,227 A | 1/1997 | Dinh | |
| 5,605,696 A | 2/1997 | Eury | |
| 5,607,475 A | 3/1997 | Cahalan et al. | |
| 5,607,687 A | 3/1997 | Bezwada et al. | |
| 5,609,629 A | 3/1997 | Fearnot | |
| 5,618,552 A | 4/1997 | Bezwada et al. | |
| 5,620,698 A | 4/1997 | Bezwada et al. | |
| 5,624,411 A | 4/1997 | Tuch | |
| 5,624,975 A | 4/1997 | Valencia | |
| 5,633,343 A | 5/1997 | Bezwada et al. | |
| 5,637,113 A | 6/1997 | Tartaglia | |
| 5,637,460 A | 6/1997 | Swan | |
| 5,639,851 A | 6/1997 | Bezwada et al. | |
| 5,641,501 A | 6/1997 | Cooper et al. | |
| 5,651,968 A | 7/1997 | Good | |
| 5,651,986 A | 7/1997 | Brem | |
| 5,656,286 A | 8/1997 | Miranda | |
| 5,660,692 A | 8/1997 | Nesburn et al. | |
| 5,674,241 A | 10/1997 | Bley | |
| 5,676,972 A | 10/1997 | Galiatsatos et al. | |
| 5,688,900 A | 11/1997 | Cooper et al. | |
| 5,703,200 A | 12/1997 | Bezwada et al. | |
| 5,705,181 A | 1/1998 | Cooper et al. | |
| 5,714,360 A | 2/1998 | Swan | |
| 5,714,551 A | 2/1998 | Bezwada et al. | |
| 5,722,424 A | 3/1998 | Engelson | |
| 5,731,087 A | 3/1998 | Fan et al. | |
| 5,741,551 A | 4/1998 | Guire | |
| 5,744,515 A | 4/1998 | Clapper | |
| 5,766,242 A | 6/1998 | Wong | |
| 5,773,019 A | 6/1998 | Ashton | |
| 5,783,502 A | 7/1998 | Swanson | |
| 5,824,049 A | 10/1998 | Ragheb | |
| 5,824,072 A | 10/1998 | Wong | |
| 5,837,313 A | 11/1998 | Ding | |
| 5,840,059 A | 11/1998 | March | |
| 5,858,653 A | 1/1999 | Duran | |
| 5,859,150 A | 1/1999 | Jamiolkowski | 525/437 |
| 5,877,224 A | 3/1999 | Brocchini | |
| 5,879,697 A | 3/1999 | Ding | |
| 5,886,026 A | 3/1999 | Hunter | |
| 5,895,407 A | 4/1999 | Jayaraman | |
| 5,897,911 A | 4/1999 | Loeffler | |
| 5,899,935 A | 5/1999 | Ding | |
| 5,902,475 A | 5/1999 | Trozera | |
| 5,919,477 A | 7/1999 | Bevan | 424/448 |
| 5,942,555 A | 8/1999 | Swanson | |
| 5,951,586 A | 9/1999 | Berg | |
| 5,958,446 A | 9/1999 | Miranda et al. | |
| 5,980,972 A | 11/1999 | Ding | |
| 5,981,298 A | 11/1999 | Chudzik | |
| 5,985,354 A | 11/1999 | Mathiowitz et al. | |
| 5,997,517 A | 12/1999 | Whitbourne | |
| 6,001,386 A | 12/1999 | Ashton | |
| 6,007,833 A | 12/1999 | Chudzik | |
| 6,013,099 A | 1/2000 | Dinh | |
| 6,042,875 A | 3/2000 | Ding | |
| 6,074,660 A | 6/2000 | Jamiolkowski et al. | |
| 6,077,698 A | 6/2000 | Swan | |
| 6,077,916 A | 6/2000 | Laurencin et al. | |
| 6,090,995 A | 7/2000 | Reich | |
| 6,096,070 A | 8/2000 | Ragheb | |
| 6,099,562 A | 8/2000 | Ding | |
| 6,110,483 A | 8/2000 | Whitbourne | |
| 6,120,536 A | 9/2000 | Ding | |
| 6,120,847 A | 9/2000 | Yang | |
| 6,121,027 A | 9/2000 | Clapper | |
| 6,129,933 A | 10/2000 | Oshlack | |
| 6,143,037 A | 11/2000 | Goldstein | |
| 6,153,252 A | 11/2000 | Hossainy | |
| 6,156,345 A | 12/2000 | Chudzik | |
| 6,156,373 A | 12/2000 | Zhong | |
| 6,214,901 B1 | 4/2001 | Chudzik | |
| 6,217,895 B1 | 4/2001 | Guo | |
| 6,235,306 B1 | 5/2001 | Miranda | |
| 6,251,136 B1 | 6/2001 | Guruwaiya | |
| 6,254,634 B1 | 7/2001 | Anderson | 623/1.42 |
| 6,258,121 B1 | 7/2001 | Yang et al. | |
| 6,284,305 B1 | 9/2001 | Ding | |
| 6,287,285 B1 | 9/2001 | Michal | |
| 6,303,148 B1 | 10/2001 | Hennink et al. | |
| 6,309,669 B1 | 10/2001 | Setterstrom et al. | |
| 6,325,807 B1 | 12/2001 | Que | |
| 6,331,313 B1 | 12/2001 | Wong | |
| 6,344,035 B1 | 2/2002 | Chudzik | |
| 6,348,152 B1 | 2/2002 | Kawahara | |
| 6,358,556 B1 | 3/2002 | Ding | |
| 6,368,586 B1 | 4/2002 | Jacob | |
| 6,395,029 B1 | 5/2002 | Levy | |
| 6,399,704 B1 | 6/2002 | Laurin | |
| 6,423,092 B2 | 7/2002 | Datta et al. | |
| 6,447,796 B1 | 9/2002 | Vook et al. | |
| 6,451,373 B1 | 9/2002 | Hossainy | |
| 6,497,691 B1 | 12/2002 | Bevins | |
| 6,506,411 B2 | 1/2003 | Hunter | |
| 6,511,749 B1 | 1/2003 | Mathiowitz et al. | |
| 6,517,520 B2 | 2/2003 | Chang | |
| 6,537,312 B2 | 3/2003 | Datta et al. | |
| 6,544,544 B2 | 4/2003 | Hunter | |
| 6,545,097 B2 | 4/2003 | Pinchuk | |
| 6,548,078 B2 | 4/2003 | Guo | |
| 6,548,569 B1 | 4/2003 | Williams et al. | |
| 6,565,872 B2 | 5/2003 | Wu et al. | |
| 6,569,441 B2 | 5/2003 | Kunz | |
| 6,585,764 B2 | 7/2003 | Wright | |
| 6,589,546 B2 | 7/2003 | Kamath | |
| 6,620,194 B2 | 9/2003 | Ding | |
| 6,653,426 B2 | 11/2003 | Alvarado | |
| 6,673,453 B2 | 1/2004 | Beavers | |
| 6,682,553 B1 | 1/2004 | Webler | |
| 6,689,803 B2 | 2/2004 | Hunter | |
| 6,713,081 B2 | 3/2004 | Nussenblatt et al. | |
| 6,730,313 B2 | 5/2004 | Helmus | |
| 6,773,888 B2 | 8/2004 | Li et al. | |
| 6,776,796 B2 | 8/2004 | Falotico et al. | |
| 6,780,424 B2 | 8/2004 | Claude | |
| 6,787,179 B2 | 9/2004 | Timm | |
| 6,790,228 B2 | 9/2004 | Hossainy | |
| 6,800,073 B2 | 10/2004 | Palasis | |
| 6,824,559 B2 | 11/2004 | Michal | |
| 6,838,493 B2 | 1/2005 | Williams et al. | |
| 6,846,841 B2 | 1/2005 | Hunter | |
| 6,867,247 B2 | 3/2005 | Williams et al. | |
| 6,872,438 B1 | 3/2005 | Allgeuer et al. | |
| 7,008,667 B2 | 3/2006 | Chudzik | |
| 7,008,979 B2 | 3/2006 | Schottman et al. | |
| 7,125,577 B2 | 10/2006 | Chappa | |
| RE39,617 E | 5/2007 | Handlin, Jr. et al. | |
| 7,285,304 B1 * | 10/2007 | Hossainy et al. | 427/2.24 |
| 2001/0029351 A1 | 10/2001 | Falotico | |
| 2002/0005206 A1 | 1/2002 | Falotico | |
| 2002/0007213 A1 | 1/2002 | Falotico | |
| 2002/0007214 A1 | 1/2002 | Falotico | |
| 2002/0007215 A1 | 1/2002 | Falotico | |
| 2002/0013298 A1 | 1/2002 | Hunter | |
| 2002/0018795 A1 | 2/2002 | Whitbourne | |
| 2002/0032434 A1 | 3/2002 | Chudzik | |
| 2002/0032477 A1 | 3/2002 | Helmus | |
| 2002/0051730 A1 | 5/2002 | Bodnar Stanko | |
| 2002/0051731 A1 | 5/2002 | Fukami | |
| 2002/0071902 A1 | 6/2002 | Ding | |

| Publication No. | Date | Name |
|---|---|---|
| 2002/0091433 A1 | 7/2002 | Ding |
| 2002/0111590 A1 | 8/2002 | Davila |
| 2002/0133183 A1 | 9/2002 | Lentz |
| 2002/0138048 A1 | 9/2002 | Tuch |
| 2002/0164374 A1 | 11/2002 | Jackson et al. |
| 2002/0165608 A1 | 11/2002 | Llanos et al. |
| 2002/0188037 A1 | 12/2002 | Chudzik |
| 2003/0031780 A1 | 2/2003 | Chudzik et al. |
| 2003/0039689 A1 | 2/2003 | Chen et al. |
| 2003/0045924 A1 | 3/2003 | Datta et al. |
| 2003/0065377 A1 | 4/2003 | Davila |
| 2003/0083646 A1 | 5/2003 | Sirhan |
| 2003/0094736 A1 | 5/2003 | Qin |
| 2003/0097088 A1 | 5/2003 | Pacetti .................. 604/19 |
| 2003/0105245 A1 | 6/2003 | Amsden .................. 525/450 |
| 2003/0157187 A1 | 8/2003 | Hunter |
| 2003/0158598 A1 | 8/2003 | Ashton et al. |
| 2003/0171496 A1 | 9/2003 | Pinchuk .................. 525/242 |
| 2003/0203000 A1 | 10/2003 | Schwarz et al. |
| 2003/0203003 A1 | 10/2003 | Nelson et al. |
| 2003/0204168 A1 | 10/2003 | Bosma .................. 604/103 |
| 2003/0207856 A1 | 11/2003 | Tremble |
| 2003/0232087 A1 | 12/2003 | Lawin |
| 2003/0232122 A1 | 12/2003 | Chappa |
| 2003/0235603 A1 | 12/2003 | Schwarz et al. |
| 2003/0236513 A1 | 12/2003 | Schwarz |
| 2003/0236514 A1 | 12/2003 | Schwarz |
| 2004/0022853 A1 | 2/2004 | Ashton |
| 2004/0030380 A1 | 2/2004 | Shulze .................. 623/1.42 |
| 2004/0033251 A1 | 2/2004 | Sparer |
| 2004/0034405 A1* | 2/2004 | Dickson .................. 623/1.11 |
| 2004/0039437 A1 | 2/2004 | Sparer |
| 2004/0047911 A1 | 3/2004 | Lyu |
| 2004/0054104 A1 | 3/2004 | Pacetti .................. 526/242 |
| 2004/0058056 A1 | 3/2004 | Osaki .................. 427/2.1 |
| 2004/0059408 A1 | 3/2004 | Alvarado .................. 623/1.13 |
| 2004/0072799 A1 | 4/2004 | Li et al. |
| 2004/0077797 A1 | 4/2004 | Asgarzadeh .................. 525/404 |
| 2004/0086542 A1 | 5/2004 | Hossainy .................. 424/423 |
| 2004/0086569 A1 | 5/2004 | Sparer et al. |
| 2004/0098118 A1 | 5/2004 | Granada et al. |
| 2004/0111144 A1 | 6/2004 | Lawin .................. 623/1.11 |
| 2004/0115273 A1 | 6/2004 | Sparer et al. |
| 2004/0117006 A1 | 6/2004 | Lewis .................. 623/1.42 |
| 2004/0117007 A1 | 6/2004 | Whitbourne .................. 623/1.42 |
| 2004/0127978 A1 | 7/2004 | Sparer et al. |
| 2004/0147999 A1 | 7/2004 | Udipi et al. |
| 2004/0170752 A1 | 9/2004 | Luthra .................. 427/2.24 |
| 2004/0175406 A1 | 9/2004 | Schwarz |
| 2004/0202691 A1 | 10/2004 | Richard .................. 424/423 |
| 2004/0224001 A1 | 11/2004 | Pacetti .................. 424/423 |
| 2004/0230298 A1 | 11/2004 | Udipi et al. |
| 2004/0234737 A1 | 11/2004 | Pacetti .................. 428/212 |
| 2004/0243225 A1 | 12/2004 | Ragheb .................. 623/1.42 |
| 2004/0253203 A1 | 12/2004 | Hossainy et al. |
| 2005/0004663 A1 | 1/2005 | Llanos et al. |
| 2005/0019371 A1 | 1/2005 | Anderson et al. |
| 2005/0025802 A1 | 2/2005 | Richard .................. 424/423 |
| 2005/0025830 A1 | 2/2005 | Bruinewoud .................. 424/472 |
| 2005/0033417 A1 | 2/2005 | Borges et al. |
| 2005/0037047 A1 | 2/2005 | Song .................. 424/423 |
| 2005/0037048 A1 | 2/2005 | Song .................. 424/423 |
| 2005/0037052 A1 | 2/2005 | Udipi .................. 424/426 |
| 2005/0042293 A1 | 2/2005 | Jackson .................. 424/486 |
| 2005/0064005 A1 | 3/2005 | Dinh .................. 424/422 |
| 2005/0064011 A1 | 3/2005 | Song .................. 424/423 |
| 2005/0064038 A1 | 3/2005 | Dinh .................. 424/486 |
| 2005/0158449 A1 | 7/2005 | Chappa |
| 2005/0281863 A1 | 12/2005 | Anderson |
| 2006/0013835 A1 | 1/2006 | Anderson |
| 2006/0057277 A1 | 3/2006 | Chappa |
| 2006/0067968 A1 | 3/2006 | Chudzik |
| 2006/0134168 A1 | 6/2006 | Chappa |

FOREIGN PATENT DOCUMENTS

| | | |
|---|---|---|
| EP | 0 294 905 A1 | 12/1988 |
| EP | 0 470 569 A1 | 2/1992 |
| EP | 0 543 653 A1 | 6/1993 |
| EP | 0 551 182 A1 | 7/1993 |
| EP | 0 568 310 A1 | 11/1993 |
| EP | 0 274 846 B1 | 2/1994 |
| EP | 0 604 022 A1 | 6/1994 |
| EP | 0 623 354 A1 | 11/1994 |
| EP | 0 706 376 B1 | 4/1996 |
| EP | 0 716 836 A1 | 6/1996 |
| EP | 0 734 721 A2 | 6/1996 |
| EP | 0 747 069 B1 | 12/1996 |
| EP | 0 879 595 A2 | 4/1998 |
| EP | 1 174 157 A1 | 4/1999 |
| EP | 0 923 953 A2 | 6/1999 |
| EP | 0945 148 A1 | 9/1999 |
| FR | 2757528 | 6/1998 |
| GB | 1 462 958 | 1/1977 |
| JP | 2036882 A2 | 2/1990 |
| JP | 7-017851 | 1/1995 |
| JP | 08033718 A2 | 2/1996 |
| JP | 09099056 A2 | 4/1997 |
| JP | 09194347 A2 | 7/1997 |
| JP | 2000511946 | 9/2000 |
| WO | WO 88/02623 | 4/1988 |
| WO | WO 89/05616 | 6/1989 |
| WO | WO 90/00887 | 2/1990 |
| WO | WO 90/01969 | 3/1990 |
| WO | WO 90/13332 | 11/1990 |
| WO | WO 91/03990 | 4/1991 |
| WO | WO 91/07154 | 5/1991 |
| WO | WO 91/10424 | 7/1991 |
| WO | WO 91/11193 | 8/1991 |
| WO | WO 91/12779 | 9/1991 |
| WO | WO 91/12846 | 9/1991 |
| WO | WO 92/00747 | 1/1992 |
| WO | WO 92/11895 | 7/1992 |
| WO | WO 92/12717 | 8/1992 |
| WO | WO 92/15286 | 9/1992 |
| WO | WO 93/06792 | 4/1993 |
| WO | WO 93/11120 | 6/1993 |
| WO | WO 93/16176 | 8/1993 |
| WO | WO 93/16687 | 9/1993 |
| WO | WO 93/17669 | 9/1993 |
| WO | WO 94/11032 | 5/1994 |
| WO | WO 94/21308 | 9/1994 |
| WO | WO 94/21309 | 9/1994 |
| WO | WO 94/24962 | 11/1994 |
| WO | WO 95/03036 | 2/1995 |
| WO | WO 95/03795 | 2/1995 |
| WO | WO 96/03164 | 2/1996 |
| WO | WO 96/03984 | 2/1996 |
| WO | WO 96/37165 | 11/1996 |
| WO | WO 96/39821 | 12/1996 |
| WO | WO 97/16544 | 5/1997 |
| WO | WO 97/34935 | 9/1997 |
| WO | WO 98/17331 | 4/1998 |
| WO | WO 98/56312 | 12/1998 |
| WO | WO 99/08717 | 2/1999 |
| WO | WO 99/16907 | 4/1999 |
| WO | WO 99/38546 | 8/1999 |
| WO | WO 99/43688 | 9/1999 |
| WO | WO 99/47129 | 9/1999 |
| WO | WO 99/47176 | 9/1999 |
| WO | WO 99/53900 | 10/1999 |
| WO | WO 99/55396 | 11/1999 |
| WO | WO 99/64086 | 12/1999 |
| WO | WO 00/12163 | 3/2000 |
| WO | WO 00/40593 | 7/2000 |

| | | |
|---|---|---|
| WO | WO 00/55396 | 9/2000 |
| WO | WO 01/00109 | 1/2001 |
| WO | WO 01/21326 | 3/2001 |
| WO | WO 01/34219 | 5/2001 |
| WO | WO 01/36008 | 5/2001 |
| WO | WO 01/44174 | 6/2001 |
| WO | WO 01/66161 | 9/2001 |
| WO | WO 01/87263 | 11/2001 |
| WO | WO 01/87342 | 11/2001 |
| WO | WO 01/87372 | 11/2001 |
| WO | WO 01/87373 | 11/2001 |
| WO | WO 01/87374 | 11/2001 |
| WO | WO 01/87375 | 11/2001 |
| WO | WO 01/87376 | 11/2001 |
| WO | WO 02/26139 | 4/2002 |
| WO | WO 02/26271 | 4/2002 |
| WO | WO 02/26281 | 4/2002 |
| WO | WO 02/78668 | 10/2002 |
| WO | WO 03/022323 | 3/2003 |
| WO | WO 03/064015 | 8/2003 |
| WO | WO 03/105920 | 12/2003 |
| WO | WO 2004/000267 | 12/2003 |
| WO | WO 2004/000384 | 12/2003 |
| WO | WO 2004/009145 | 1/2004 |
| WO | WO 2004/014447 | 2/2004 |
| WO | WO 2004/014448 | 2/2004 |
| WO | WO 2004/014450 | 2/2004 |
| WO | WO 2004/014451 | 2/2004 |
| WO | WO 2004/043441 | 5/2004 |
| WO | WO 2004/098565 | 11/2004 |
| WO | WO 2005/097228 | 10/2005 |

OTHER PUBLICATIONS

Brown, L.R., et al., "Characterization of glucose-mediated insulin release from implantable polymers", J Pharm Sci Dec. 1996; 85 (12): 1341-1345.

Catz P; et al., "In vitro evaluations of transdermal levonorgestrel", Drug Des Deliv, May 1990; 6 (1): 49-60.

Edelman, E.R. et al., "C-myc in vasculoproliferative disease", Circ Res Feb. 1995; 76(2): 176-82.

Eliaz, R., et al., "Long-term protection against the effects of tumor necrosis factor by controlled delivery of the soluble p55 TNF receptor", Cytokine, Jun. 1996; 8(6): 482-7.

Flemming, T.F., et al., "Adjunctive controlled topical application of tetracycline HCl in the treatment of localized persistent or recurrent periodontitis. Effects on clinical parameters and elastase-alpha 1-proteinase inhibitor in gingival crevicular fluid", J. Clin Periodontol Oct. 1996; 23 (10):914-21.

Folkman, J, "How the field controlled-release technology began, and its central role in the development of angiogenesis research", Biomaterials, Nov. 1990; 11 (9): 615-8.

Lesser, G.J., et al., "In vitro and in vivo studies of subcutaneous hydromorphone implants designed for the treatment of cancer pain", Pain, May-Jun. 1996; 65 (2-3): 265-72.

Lopez, J.J., et al., "Angiogenic potential of perivascularly delivered aFGF in a porcine model of chronic myocardial ischemia", Am J Physiol Mar. 1998; 274 (3 Pt 2): H930.

Ozaki, H., et al., "Intravitreal sustained release of VEGF causes retinal neovascularization in rabbits and breakdown of the blood-retinal barrier in rabbits and primates", Exp Eye Res, 1997, 64, 505-17.

Sellke, F.W., et al., "Angiogenesis induced by acidic fibroblast growth factor as an alternative method of revascularization for chronic myocardial ischemia", Surgery Aug. 1996; 120 (2): 182-8.

Suzuki, T. et al., "Stent-based delivery of sirolimus reduces neointimal formation in a porcine coronary model", Circulation, 2001; 104: 1188-1193.

Jafary, F, et al., "Point-Counterpoint: Drug Eluting Stent Euphoria: A Revolutionary Step or Misguided Euphoria?" http://www.medscape.com/viewarticle/442687, printed Oct. 15, 2002.

Morice et al., "A Randomized Comparison of a Sirolimus-Eluting Stent With a Standard Stent for Coronary Revascularaization" N. Engl. J. Med., vol. 346, No. 23, Jun. 6, 2002, pp. 1773-1780.

Raman et al., "Coated Stents: Local Pharmacology", Semin. Intervent. Cardiol., 1998; 3:133-137.

Whelan et al., "Mechanisms of Drug Loading and Release Kinetics", Semin. Intervent. Cardiol., 1998; 3:127-131.

Klugherz, et al., "Twenty-eight-day Efficacy and Phamacokinetics of the sirolimus-eluting stent", Coronary Artery Disease, 2002, vol. 13, No. 3, pp. 183-188.

Regar, et al., "Stent Development and Local Drug Delivery", British Medical Bulletin 2001; 59: 227-248.

Serruys, et al., "Rapamycin Eluting Stent: the Onset of a New Era in Interventional Cardiology", Heart 2002; 87:305-307.

Friling, R., et al., "A role of transforming growth factor-beta 1 in the control of corneal neovascularization", In Vivo 10, 59-64 (1996).

Goodson, J.M., et al., "Clinical responses following periodontal treatment by local drug delivery", J Periodontal Nov. 1985; 56 (11 Suppl): 81-7.

Huland, E., et al., "In Vivo system to detect long-term continuous release of bioactive interleukin-2 by immunopharmacological depot preparations in nude mice with human tumors", J. Cancer Res. Clin. Oncol. (1995) 121:285-290.

Lees, V.C., et al., "Angiogenesis in a delayed revascularization model is accelerated by angiogenic oligosaccharide of hyaluronan", Lab Invest, 1995, vol. 73, No. 9, pp. 259-266.

Virmani, R., MD et al., "Mechanism of Late In-Stent Restenosis After Implantation of a Paclitaxel Derivate-Eluting Polymer Stent System in Humans", Circulation, 2002; 106:2649-2651.

Grube, E., MD, et al., "Six- and Twelve-Month Results From a Randomized, Double-Blind Trial on a Slow-Release Paclitaxel-Eluting Stent for De Novo Coronary Lesions", Circulation, 2003; 107: 38-42.

Serruys, P., MD, PhD, "Final Action Results (Actinomycin D) Test", (Sep. 2002).

Trevino, M., "Results for drug-eluting stents disappoint, Diagnostic Imaging Online", (Apr. 25, 2002), http://www.dimag.com/dinews/2002042501.shtml.

Jampel, H. D., MD, et al., "In Vitro Release of Hydrophobic Drugs From Polyanhydride Disks", Ophthalmic Surgery, Nov. 1991, vol. 22, No. 11, pp. 676-680.

Sousa, J. Eduardo, MD, PhD, et al., "Clinical Cardiology: New Frontiers, New Frontiers in Cardiology, Drug-Eluting Stents: Part I", Circulation 2003; 107:2274-2279.

O'Keefe, Jr., J., MD, et al., "Ineffectiveness of Colchicine for the Prevention of Restenosis After Coronary Angioplasty", JACC, vol. 19, No. 7, Jun. 1992: 1597-1600.

Hirata, S., et al., Inhibition of In Vitro Vascular Endothelial Cell Proliferation and In Vivo Neovascularization by Low-dose Methotrexate, *Arthritis and Rheumatism*, vol. 32, No. 9 (Sep. 1989), p. 1065-1073.

Coronary Artery Disease, vol. 3, No. 3, (Mar. 1992), pp. 237-248.

Lambert, T., et al., "A New Method for Arterial Drug Delivery via Removable Stent", *JACC* vol. 21 No. 2, 834-2, (Feb. 1993).

Cox, D., MD, et al., "Effect of local delivery of heparin and methotrexate on neointimal proliferation in stented porcine coronary arteries", Coronary Artery Disease, Mar. 1992: vol. 3, No. 3, pp. 237-248.

Pitt, C.G., et al., "Progress in Contraceptive Delivery Systems", (Hafez, E.S.E, van Os, W., editors, vol. 1, pp. 17-18, MTP Press, Lancaster (1980).

Bartoli, M., et al., "In vitro and in vivo antitumoral activity of free, and encapsulated taxol", *J. Microencapsulation*, vol. 7, No. 2, 191-197 (1990).

The 2nd International Coronary Stenting Summit, Mar. 1-2, 1991.

Cox, David A., et al., "Local Delivery of Heparin and Methotrexate Fails to Inhibit In Vivo Smooth Muscle Cell Proliferation, *Supplement to Circulation*, Abstracts from the 64th Scientific Sessions," vol. 84, No. 4, Oct. 1991.

Shen et al., "Polymer-Supported Lipid Bilayers on Benzophenone-Modified Substrates", *Biomacromolecules* 2001, vol. 2, No. 1, pp. 70-79.

Machine translation of Voisard, R. et al., "Suche nach neuen Strategien zur Verhutung von Restenosen nach Angioplatie: Der Effekt von Cytostatika auf die Migrationsfahigkeit von Restenosierenden Plaquezellen des Menschen in Vitro," Vasa Suppl. 1992; 35:132-133.

Kornowski, R. et al., Slow-Release Taxol Coated GRII Stents Reduce Neointima Formation in a Porcine Coronary In-Stent Restenosis Model (Abstr.) Circulation. 1997; 96:341.

Drachman, D. et al., "Sustained Stent-Based Delivery of Paclitaxel Arrests Neointernal Thickening and Cell Proliferation," 71st Scientific Sessions of the American Heart Association, San Diego, California, Nov. 1998.

Hermans, W. R. M. et al., "Prevention of Restenosis after Percutaneous Transluminal Coronary Angioplasty: The Search for a Magic Bullet", Am. Heart Journal, vol. 122, No. 1, pt. 1, 171-187 (1991).

Non-Final Office Action mailed Aug. 1, 2008 in co-pending U.S. Appl. No. 11/099,935, "Coating Compositions for Bioactive Agents," (16 pages).

Non-Final Office Action mailed Aug. 6, 2008 in co-pending U.S. Appl. No. 11/099,796, "Coating Compositions for Bioactive Agents," (14 pages).

Non-Final Office Action mailed Aug. 1, 2008 in co-pending U.S. Appl. No. 11/099,911, "Coating Compositions for Bioactive Agents," (14 pages).

Non-Final Office Action mailed Jul. 24, 2008 in co-pending U.S. Appl. No. 11/099,939, "Coating Compositions for Bioactive Agents," (13 pages).

Final Office Action mailed Mar. 3, 2009, in co-pending U.S. Appl. No. 11/099,939, "Coating Compositions for Bioactive Agents," (19 pages).

Non-Final Office Action mailed Feb. 23, 2009, in co-pending U.S. Appl. No. 11/099,935, "Coating Compositions for Bioactive Agents," (20 pages).

Non-Final Office Action mailed Feb. 23, 2009 in co-pending U.S. Appl. No. 11/099,911, "Coating Compositions for Bioactive Agents," (18 pages).

Sartomer Application Bulletin, 2005, download from http://www.sartomer.com/TechLit/4932.pdf. on Feb. 25, 2008, (1 page).

* cited by examiner

Figure 1

US 7,541,048 B2

COATING COMPOSITIONS FOR BIOACTIVE AGENTS

RELATED APPLICATIONS

This application claims the benefit of U.S. Provisional Application Ser. No. 60/559,821, titled Coating Compositions for Bioactive Agents, filed Apr. 6, 2004, the contents of which are hereby incorporated by reference. This application is related to PCT Application Ser. No. PCT/US2005/011406, filed Apr. 6, 2005, titled Coating Compositions for Bioactive Agents and identified, as well as PCT Application Ser. No. PCT/US2005/011655, filed Apr. 6, 2005, titled Coating Compositions for Bioactive Agents and identified by , the contents of both of which are hereby incorporated by reference.

TECHNICAL FIELD

In one aspect, the present invention relates to a method of treating implantable medical devices with coating compositions to provide for the controlled release of bioactive (e.g., pharmaceutical) agents from the surface of the devices under physiological conditions. In another aspect, the invention relates to the coating compositions, per se. In yet another aspect, the invention relates to devices or surfaces coated with such compositions. In yet another aspect, the present invention relates to the local administration of bioactive agents for the prevention and treatment of diseases, such as vascular and ocular diseases.

BACKGROUND OF THE INVENTION

Many surgical interventions require the placement of a medical device into the body. One prevalent surgical intervention often requiring such a device is percutaneous transluminal coronary angioplasty ("PTCA"). Many individuals suffer from circulatory disease caused by a progressive blockage of the blood vessels, which often leads to hypertension, ischemic injury, stroke, or myocardial infarction. Percutaneous transluminal coronary angioplasty is a medical procedure performed to increase blood flow through a damaged artery and is now the predominant treatment for coronary vessel stenosis. The increasing use of this procedure is attributable to its relatively high success rate and its minimal invasiveness compared with coronary bypass surgery. A limitation associated with PTCA is the abrupt closure of the vessel which can occur soon after angioplasty. Insertion of small spring-like medical devices called stents into such damaged vessels has proved to be a better approach to keep the vessels open as compared to systemic pharmacologic therapy.

While often necessary and beneficial for treating a variety of medical conditions, metal or polymeric devices (e.g., stents, catheters . . . ), after placement in the body, can give rise to numerous physiological complications. Some of these complications include: increased risk of infection; initiation of a foreign body response resulting in inflammation and fibrous encapsulation; and initiation of a detrimental wound healing response resulting in hyperplasia and restenosis. These problems have been particularly acute with the placement of stents in damaged arteries after angioplasty.

One promising approach is to provide the device with the ability to deliver bioactive agents in the vicinity of the implant. By doing so, some of the harmful effects associated with the implantation of medical devices can be diminished. Thus, for example, antibiotics can be released from the surface of the device to minimize the possibility of infection, and antiproliferative drugs can be released to inhibit hyperplasia.

Another benefit to the local release of bioactive agents is the avoidance of toxic concentrations of drugs encountered when given systemically at sufficiently high doses to achieve therapeutic concentrations at the site where they are needed.

Although the potential benefit from using such bioactive agent-releasing medical devices is great, development of such medical devices has been slow. Progress has been hampered by many challenges, including: 1) the requirement, in some instances, for long term (i.e., at least several weeks) release of bioactive agents; 2) the need for a biocompatible, non-inflammatory device surface; 3) the demand for significant durability (and particularly, resistance to delamination and cracking), particularly with devices that undergo flexion and/or expansion when being implanted or used in the body; 4) concerns regarding the ability of the device to be manufactured in an economically viable and reproducible manner; and 5) the requirement that the finished device can be sterilized using conventional methods.

Implantable medical devices capable of delivering medicinal agents from hydrophobic polymer coatings have been described. See, for instance, U.S. Pat. Nos. 6,214,901; 6,344,035; U.S. Publication No. 2002-0032434; U.S. Publication No. 2002-0188037; U.S. Publication No. 2003-0031780; U.S. Publication No. 2003-0232087; U.S. Publication No. 2003-0232122; PCT Publication No. WO 99/55396; PCT Publication No. WO 03/105920; PCT Publication No. WO 03/105918; PCT Publication No. WO 03/105919 which collectively disclose, inter alia, coating compositions having a bioactive agent in combination with a polymer component such as polyalkyl(meth)acrylate or aromatic poly(meth)acrylate polymer and another polymer component such as poly (ethylene-co-vinyl acetate) for use in coating device surfaces to control and/or improve their ability to release bioactive agents in aqueous systems.

SUMMARY OF THE INVENTION

The present invention provides a coating composition, and related methods for preparing and using the coating composition to coat a surface with a bioactive agent, for instance to coat the surface of an implantable medical device in a manner that permits the surface to release the bioactive agent over time when implanted in vivo.

The coating composition of this invention comprises one or more bioactive agents in combination with a plurality of polymers, including: (a) a first polymer component comprising ethylene copolymers with other alkylenes; and (b) a second polymer component comprising one or more polymers selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Applicants have discovered a group of first polymers that when used in combination with one or more second polymers can each meet or exceed the variety of criteria required of a composition of this invention, including in terms of its formulation, delivery, and/or coated characteristics.

In various embodiments, with regard to its formulation, a coating composition of this invention is provided in the form of a true solution by the use of one or more solvents. Such solvents, in turn, are not only capable of dissolving the polymers and bioactive agent in solution, as compared to dispersion or emulsion, but they are also sufficiently volatile to permit the composition to be effectively applied to a surface (e.g., as by spraying) and quickly removed (e.g., as by drying)

to provide a stable and desirable coated composition. In turn, the coated composition is itself homogeneous, with the first and second polymers effectively serving as cosolvents for each other, and bioactive agent substantially equally sequestered within them both.

In various embodiments of the present invention, the ability to form a true solution using the claimed polymer combinations is desired when considering the inclusion of potentially significant amounts of bioactive agent with the polymer blend. In various embodiments of the present invention, the coating composition is not only in the form of a true solution, but one in which bioactive agent is present at saturated or supersaturated levels. Without intending to be bound by theory, it appears that it is by virtue of the ability to achieve such solutions, that release of the bioactive agent from the coated composition is best accomplished and facilitated. In turn, it appears that the release of bioactive agent from such a system is due, at least in part, to its inherent instability within the coated composition itself, coupled with its physical/chemical preference for surrounding tissues and fluids. In turn, those skilled in the art will appreciate the manner in which the various ingredients and amounts in a composition of this invention can be adjusted to provide desired release kinetics and for any particular bioactive agent, solvent and polymer combination.

In some embodiments of the present invention, with regard to its delivery, a composition of this invention meets or exceeds further criteria in its ability to be sterilized, stored, and delivered to a surface in a manner that preserves its desired characteristics, yet using conventional delivery means, such as spraying. In various embodiments, such delivery involves spraying the composition onto a device surface in a manner that avoids or minimizes phase separation of the polymer components.

Finally, and with regard to its coated characteristics, a composition of this invention permits polymer ratios to be varied in a manner that provides not only an optimal combination of such attributes as biocompatibility, durability, and bioactive agent release kinetics, but also that provides a coated composition that is homogeneous, and hence substantially optically clear upon microscopic examination. Even more surprisingly, various compositions of this invention will provide these and other features, with or without optional pretreatment of a metallic surface. The ability to achieve or exceed any of these criteria, let alone most if not all of them, was not expected.

In turn, compositions of the present invention provide properties that are comparable or better than those obtained with previous polymer blend compositions. This, in turn, provides a variety of new and further opportunities, including with respect to both the type and concentration of bioactive agents that can be coated, as well as the variety of medical devices, and surfaces, themselves. In turn, the present invention also provides a combination that includes a medical device coated with a composition of this invention, as well as a method of preparing and using such a combination.

BRIEF DESCRIPTION OF THE FIGURES

FIG. 1 depicts a graph illustrating the cumulative bioactive agent release profiles for coating compositions according to the present invention applied to stents, as described in Example 1.

DETAILED DESCRIPTION

Without intending to be bound by theory, it appears that suitable first polymers for use in a composition of this invention provide an optimal combination of such properties as glass transition temperature ($T_g$) and diffusion constant for the particular bioactive agent of choice. Along with melting temperature ($T_m$), $T_g$ is an important parameter of a given polymer (including copolymer), and particularly amorphous polymers, that can be used to characterize its properties over a wide temperature range. A polymer is typically brittle at temperatures below its $T_g$, and flexible at temperatures above. Both $T_m$ and $T_g$ can be affected by such things as polymer structure and backbone flexibility, molecular weight, attractive forces, and pressure. For random copolymers and compatible polymer blends, only a single $T_g$ is observed, usually lying intermediate between the $T_g$ of the corresponding pure homopolymers. Different $T_g$'s are exhibited for incompatible polymer blends, and between the microdomains of block copolymers with mutually incompatible blocks. $T_g$ can be measured by any suitable technique, e.g., dilatometry, refractive index, differential scanning calorimetry, dynamic mechanical measurement, and dielectric measurement.

Various second polymers (e.g., poly (n-butyl methacrylate)) of the present composition generally provide a $T_g$ in the range of room to body temperature (e.g., from about 20° C. to about 40° C.), and hence tend to be somewhat stiffer polymers, in turn, providing a slower diffusion constant for a number of bioactive agents. Applicants have discovered the manner in which certain new polymers can be used as a first polymer component, to essentially balance, or temper the desired properties of the second polymer. Such first polymers will generally provide a lower glass transition temperature (e.g., below room temperature, and, in some embodiments, in the range of about 0° C. or less), together with a relatively high diffusion constant for the bioactive agent. By appropriately combining the two polymers with bioactive agent, those skilled in the art, given the present description, will be able to vary both the selection and ratios of first and second polymers, in order to determine an optimal combination of physical and mechanical properties, including bioactive agent diffusion and release kinetics, as well as durability and tenacity of the coating itself upon a particular surface, that best fits their particular needs.

Hence embodiments of the first polymer of this invention will provide an optimal combination of glass transition temperature (e.g., at or lower than that of the second polymer), compatibility with the bioactive agent of choice, acceptable solubility in the solvents of choice, as well as commercial availability and cost.

The term "coating composition", as used herein, will refer to one or more vehicles (e.g., solutions, mixtures, emulsions, dispersions, blends, etc.) used to effectively coat a surface with bioactive agent, first polymer component and/or second polymer component, either individually or in any suitable combination.

The term "coated composition" will refer to the effective combination, upon the surface of a device, of bioactive agent, first polymer component and second polymer component, whether formed as the result of one or more coating vehicles or in one or more layers and/or steps.

Unless defined otherwise, the term "coating" will refer to the effective combination of bioactive agent, first polymer component and second polymer component, independent of the device surface, and whether formed as the result of one or more coating vehicles or in one or more layers.

Unless otherwise indicated, the term "molecular weight" and all polymeric molecular weights described herein are "weight average" molecular weights ("Mw"). As used herein "weight average molecular weight" or $M_w$, is an absolute method of measuring molecular weight and is particularly useful for measuring the molecular weight of a polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., Contemporary Polymer Chemistry; pg 271 (1990).

As described and exemplified herein, a resultant composition can be coated using a plurality of individual steps or layers, including for instance, an initial layer having only bioactive agent (or bioactive agent with one or both of the polymer components), over which are coated one or more additional layers containing suitable combinations of bioactive agent, first polymer component and/or second polymer component, the combined result of which is to provide a coated composition of the invention. In turn, and in various embodiments, the invention further provides a method of reproducibly controlling the release (e.g., elution) of a bioactive agent from the surface of a medical device implanted in vivo. Those skilled in the art will appreciate the manner in which the combined effect of these various layers can be used and optimized to achieve various effects in vivo. In addition, the surface to which the composition is applied can itself be pretreated in a manner sufficient to improve attachment of the composition to the underlying (e.g., metallic) surface. Examples of such pretreatments include the use of compositions such as Parylene™ coatings, as described herein. Additional examples of such pretreatments include silane coupling agents, photografted polymers, epoxy primers, polycarboxylate resins, and physical roughening of the surface. It is further noted that the pretreatment compositions may be used in combination with each other or may be applied in separate layers to form a pretreatment coating on the surface of the medical device.

While not intending to be bound by theory, the release kinetics of the bioactive agent in vivo are thought to generally include both a short term ("burst") release component, within the order of minutes to hours after implantation, and a longer term release component, which can range from on the order of hours to days or even months or years of useful release.

Additionally, the ability to coat a device in the manner of the present invention provides greater latitude in the composition of various coating layers, e.g., permitting more or less of the second polymer component (i.e., poly(alkyl (meth) acrylate) and/or poly(aromatic (meth)acrylate)) to be used in coating compositions used to form different layers (e.g., as a topcoat layer). This, in turn, provides the opportunity to further control release and elution of the bioactive agent from the overall coating.

The coating composition and method can be used to control the amount and rate of bioactive agent (e.g., drug) release from one or more surfaces of implantable medical devices. In various embodiments, the method employs a mixture of hydrophobic polymers in combination with one or more bioactive agents, such as a pharmaceutical agent, such that the amount and rate of release of agent(s) from the medical device can be controlled, e.g., by adjusting the relative types and/or concentrations of hydrophobic polymers in the mixture. For a given combination of polymers, for instance, this approach permits the release rate to be adjusted and controlled by simply adjusting the relative concentrations of the polymers in the coating mixture. This provides an additional means to control rate of bioactive agent release besides the conventional approach of varying the concentration of bioactive agent in a coated composition.

Some embodiments of the invention include a method of coating a device comprising the step of applying the composition to the device surface under conditions of controlled relative humidity (at a given temperature), for instance, under conditions of increased or decreased relative humidity as compared to ambient humidity. Humidity can be "controlled" in any suitable manner, including at the time of preparing and/or using (as by applying) the composition, for instance, by coating the surface in a confined chamber or area adapted to provide a relative humidity different than ambient conditions, and/or by adjusting the water content of the coating or coated composition itself. Without intending to be bound by theory, it appears that the elution rate of a bioactive agent from a coating composition generally increases as relative humidity increases.

Some coating compositions of this invention includes a mixture of two or more polymers having complementary physical characteristics, and a bioactive agent or agents applicable to the surface of an implantable medical device. The device can be of any suitable type or configuration, and may be one that undergoes flexion and/or expansion upon implantation or use, as in the manner of a stent or catheter. The applied coating composition is cured (e.g., by solvent evaporation) to provide a tenacious and flexible bioactive-releasing composition on the surface of the medical device. Such coating compositions are particularly well suited for devices that are themselves sufficiently small, or have portions that are sufficiently small (as in the struts of an expandable stent or the twists of an ocular coil), to permit the coated composition to form a contiguous, e.g., circumferential, coating, thereby further improving the ability of the coating to remain intact (e.g., avoid delamination).

The complementary polymers are selected such that a broad range of relative polymer concentrations can be used without detrimentally affecting the desirable physical characteristics of the polymers. By use of the polymer combinations (including mixtures and blends) of the invention the bioactive release rate from a coated medical device can be manipulated by adjusting the relative concentrations of the polymers.

In some embodiments, the present invention relates to a coating composition and related method for coating an implantable medical device which undergoes flexion and/or expansion upon implantation. However it is noted that the coating composition may also be utilized with medical devices that have minimal or do not undergo flexion and/or expansion. The structure and composition of the underlying device can be of any suitable, and medically acceptable, design and can be made of any suitable material that is compatible with the coating itself. The natural or pretreated surface of the medical device is provided with a coating containing one or more bioactive agents.

A first polymer component of this invention provides an optimal combination of similar properties, and particularly when used in admixture with the second polymer component. In various embodiments, first polymers include ethylene copolymers with other alkylenes. Examples of suitable polymers are commercially available from sources such as Sigma-Aldrich.

First polymers for use in this invention may include ethylene copolymers with other alkylenes, which in turn, can include straight chain and branched alkylenes, as well as substituted or unsubstituted alkylenes. Examples include copolymers prepared from alkylenes that comprise from 3 to 8 branched or linear carbon atoms, inclusive, optionally alkylene groups that comprise from 3 to 4 branched or linear carbon atoms, inclusive, and in some embodiments, the alkylene group contains 3 carbon atoms (e.g., propylene). In various embodiments, the other alkylene is a straight chain alkylene (e.g., 1-alkylene).

Various copolymers of this type can comprise from about 20% to about 90% (based on moles) of ethylene, and in some embodiments, from about 35% to about 80% (mole) of ethylene. Such copolymers will have a molecular weight of between about 30 kilodaltons to about 500 kilodaltons. Examples of various copolymers are selected from the group consisting of poly(ethylene-co-propylene), poly(ethylene-co-1-butene), polyethylene-co-1-butene-co-1-hexene) and/or poly(ethylene-co-1-octene).

Examples of various copolymers that may be utilized in the present invention include poly(ethylene-co-propylene) random copolymers in which the copolymer contains from about 35% to about 65% (mole) of ethylene; and in some embodiments, from about 55% to about 65% (mole) ethylene, and the molecular weight of the copolymer is from about 50 kilodaltons to about 250 kilodaltons, in some embodiments from about 100 kilodaltons to about 200 kilodaltons.

Copolymers of this type can optionally be provided in the form of random terpolymers prepared by the polymerization of both ethylene and propylene with optionally one or more additional diene monomers, such as those selected from the group consisting of ethylidene norborane, dicyclopentadiene and/or hexadiene. Various terpolymers of this type can include up to about 5% (mole) of the third diene monomer.

Other examples of suitable first copolymers of this type are commercially available from sources such as Sigma-Aldrich and include the following products. Suitable copolymers of this type and their related descriptions may be found in the 2003-2004 Aldrich Handbook of Fine Chemicals and Laboratory Equipment, the entire contents of which are incorporated by reference herein. Examples of such copolymers include, but are not limited to poly(ethylene-co-propylene), poly(ethylene-co-1-butene), poly(ethylene-co-1-butene-co-1-hexene), poly(ethylene-co-1-octene) and poly(ethylene-co-propylene-co-5-methylene-2-norborene).

A second polymer component of this invention provides an optimal combination of various structural/functional properties, including hydrophobicity, durability, bioactive agent release characteristics, biocompatibility, molecular weight, and availability. In one such an embodiment, the composition in some embodiments comprises at least one second polymer component selected from the group consisting of poly(alkyl (meth)acrylates) and poly(aromatic (meth)acrylates).

In various embodiments, the second polymer component is a poly(alkyl)methacrylate, that is, an ester of a methacrylic acid. Examples of suitable poly(alkyl (meth)acrylates) include those with alkyl chain lengths from 2 to 8 carbons, inclusive, and with molecular weights from 50 kilodaltons to 900 kilodaltons. In various embodiments the polymer mixture includes a poly(alkyl (meth)acrylate) with a molecular weight of from about 100 kilodaltons to about 1000 kilodaltons, optionally from about 150 kilodaltons to about 500 kilodaltons, and in some embodiments from about 200 kilodaltons to about 400 kilodaltons. An example of one embodiment of a second polymer is poly (n-butyl methacrylate). Examples of other second polymers are poly(n-butyl methacrylate-co-methyl methacrylate, with a monomer ratio of 3:1, poly(n-butyl methacrylate-co-isobutyl methacrylate, with a monomer ratio of 1:1 and poly(t-butyl methacrylate). Such polymers are available commercially (e.g., from Sigma-Aldrich, Milwaukee, Wis.) with molecular weights ranging from about 150 kilodaltons to about 350 kilodaltons, and with varying inherent viscosities, solubilities and forms (e.g., as slabs, granules, beads, crystals or powder).

Examples of suitable poly(aromatic (meth)acrylates) include poly(aryl (meth)acrylates), poly(aralkyl (meth)acrylates), poly(alkaryl (meth)acrylates), poly(aryloxyalkyl (meth)acrylates), and poly (alkoxyaryl (meth)acrylates). Such terms are used to describe polymeric structures wherein at least one carbon chain and at least one aromatic ring are combined with (meth)acrylic groups, typically esters, to provide a composition of this invention. For instance, and more specifically, a poly(aralkyl (meth)acrylate) can be made from aromatic esters derived from alcohols also containing aromatic moieties, such as benzyl alcohol. Similarly, a poly (alkaryl (meth)acrylate) can be made from aromatic esters derived from aromatic alcohols such as p-anisole. Suitable poly(aromatic (meth)acrylates) include aryl groups having from 6 to 16 carbon atoms and with molecular weights from about 50 to about 900 kilodaltons. Examples of suitable poly (aryl (meth)acrylates) include poly(9-anthracenyl methacrylate), poly(chlorophenyl acrylate), poly(methacryloxy-2-hydroxybenzophenone), poly(methacryloxybenzotriazole), poly(naphthyl acrylate), poly(naphthylmethacrylate), poly-4-nitrophenylacrylate, poly(pentachloro(bromo, fluoro) acrylate) and methacrylate, poly(phenyl acrylate) and poly (phenyl methacrylate). Examples of suitable poly(aralkyl (meth)acrylates) include poly(benzyl acrylate), poly(benzyl methacrylate), poly(2-phenethyl acrylate), poly(2-phenethyl methacrylate) and poly(1-pyrenylmethyl methacrylate). Examples of suitable poly(alkaryl(meth)acrylates) include poly(4-sec-butylphenyl methacrylate), poly(3-ethylphenyl acrylate), and poly(2-methyl-1-naphthyl methacrylate). Examples of suitable poly(aryloxyalkyl (meth)acrylates) include poly(phenoxyethyl acrylate), poly(phenoxyethyl methacrylate), and poly(polyethylene glycol phenyl ether acrylate) and poly(polyethylene glycol phenyl ether methacrylate) with varying polyethylene glycol molecular weights. Examples of suitable poly(alkoxyaryl(meth)acrylates) include poly(4-methoxyphenyl methacrylate), poly(2-ethoxyphenyl acrylate) and poly(2-methoxynaphthyl acrylate).

Acrylate or methacrylate monomers or polymers and/or their parent alcohols are commercially available from Sigma-Aldrich (Milwaukee, Wis.) or from Polysciences, Inc, (Warrington, Pa.).

Optionally, the coating composition may include one or more additional polymers in combination with the first and second polymer components, the additional polymers being, for example, selected from the group consisting of (i) poly (alkylene-co-alkyl(meth)acrylates), (ii) polybutenes, (iii) diolefin derived non-aromatic polymers and copolymers (iv) aromatic group-containing copolymers, (v) epichlorohydrin-containing polymers and (vi) poly (ethylene-co-vinyl acetate). In some embodiments, the additional polymers may act as substitutes for a portion of the first polymer. For example, the additional polymers may substitute up to about 25% of the first polymer. In other embodiments, the additional polymers may substitute up to about 50% of the first polymer.

Suitable poly(alkylene-co-alkyl(meth)acrylates) include those copolymers in which the alkyl groups are either linear or branched, and substituted or unsubstituted with non-interfering groups or atoms. In various embodiment of the present invention, the alkyl groups comprise from 1 to 8 carbon atoms, inclusive, and in some embodiments, from 1 to 4 carbon atoms, inclusive. In one embodiment, the alkyl group is methyl.

In turn, copolymers that include such alkyl groups in some embodiments comprise from about 15% to about 80% (wt) of alkyl acrylate. When the alkyl group is methyl, the polymer in various embodiments contains from about 20% to about 40% methyl acrylate, and in some embodiments from about 25 to about 30% methyl acrylate. When the alkyl group is ethyl, the polymer in some embodiments contains from about 15% to about 40% ethyl acrylate, and when the alkyl group is butyl, the polymer in various embodiments contains from about 20% to about 40% butyl acrylate.

The alkylene groups are selected from ethylene and/or propylene, and in one embodiment, the alkylene group is ethylene. In various embodiments, the (meth)acrylate comprises an acrylate (i.e., no methyl substitution on the acrylate group). Various copolymers provide a molecular weight (Mw) of about 50 kilodaltons to about 500 kilodaltons, and in some embodiments, Mw is 50 kilodaltons to about 200 kilodaltons.

The glass transition temperature for these copolymers varies with ethylene content, alkyl length on the (meth)acrylate and whether the first copolymer is an acrylate or methacrylate. At higher ethylene content, the glass transition temperature tends to be lower, and closer to that of pure polyethylene (−120° C.). A longer alkyl chain also lowers the glass transition temperature. A methyl acrylate homopolymer has a glass transition temperature of about 10° C. while a butyl acrylate homopolymer has one of −54° C.

Copolymers such as poly(ethylene-co-methyl acrylate), poly(ethylene-co-butyl acrylate) and poly(ethylene-co-2-ethylhexyl acrylate) copolymers are available commercially from sources such as Atofina Chemicals, Inc., Philadelphia, Pa., and can be prepared using methods available to those skilled in the respective art.

Other examples of suitable copolymers of this type are commercially available from sources such as Sigma-Aldrich and include, but are not limited to, poly(ethylene-co-methyl acrylate), poly(ethylene-co-ethyl acrylate), and poly(ethylene-co-butyl acrylate).

"Polybutenes" suitable for use as additional polymers include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In various embodiments, the polybutene contains at least about 90% (wt) of isobutylene or 1-butene, and in some embodiments, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol).

In some embodiments, the polybutene has a molecular weight between about 100 kilodaltons and about 1,000 kilodaltons, and may be between about 150 kilodaltons and about 600 kilodaltons, and in other embodiments, between about 150 kilodaltons and about 250 kilodaltons. In other embodiments, the polybutene has a molecular weight between about 150 kilodaltons and about 1,000 kilodaltons, optionally, between about 200 kilodaltons and about 600 kilodaltons, and further optionally, between about 350 kilodaltons and about 500 kilodaltons. Polybutenes having a molecular weight greater than about 600 kilodaltons, including greater than 1,000 kilodaltons are available but are expected to be more difficult to work with. Other examples of suitable copolymers of this type are commercially available from sources such as Sigma-Aldrich.

Other examples of suitable copolymers of this type are commercially available from sources such as Sigma-Aldrich.

Additional polymers may also include diolefin-derived, non-aromatic polymers and copolymers, including those in which the diolefin monomer used to prepare the polymer or copolymer is selected from butadiene ($CH_2=CH-CH=CH_2$) and/or isoprene ($CH_2=CH-C(CH_3)=CH_2$). A butadiene polymer can include one or more butadiene monomer units which can be selected from the monomeric unit structures (a), (b), or (c):

An isoprene polymer can include one or more isoprene monomer units which can be selected from the monomeric unit structures (d), (e), (f), or (g):

In some embodiments, the additional polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes containing polymerized cis-, trans- and/or 1,2-monomer units, and in some embodiments, a mixture of all three co-polymerized monomer units, and polyisoprenes containing polymerized cis-1,4- and/or trans-1,4-monomer units, polymerized 1,2-vinyl monomer units, polymerized 3,4-vinyl monomer units and/or others as described in the Encyclopedia of Chemical Technology, Vol. 8, page 915 (1993), the entire contents of which is hereby incorporated by reference.

Alternatively, the additional polymer is a copolymer, including graft copolymers, and random copolymers based on a non-aromatic mono-olefin co-monomer such as acrylonitrile, an alkyl (meth)acrylate and/or isobutylene. In various embodiments, when the mono-olefin monomer is acrylonitrile, the interpolymerized acrylonitrile is present at up to about 50% by weight; and when the mono-olefin monomer is isobutylene, the diolefin monomer is isoprene (e.g., to form what is commercially known as a "butyl rubber"). In some embodiments, the polymers and copolymers have a Mw between about 50 kilodaltons and about 1,000 kilodaltons. In other embodiments, the polymers and copolymers have a Mw between about 100 kilodaltons and about 450 kilodaltons. In yet other embodiments the polymers and copolymers have a Mw between about 150 kilodaltons and about 1,000 kilodaltons, and optionally between about 200 kilodaltons and about 600 kilodaltons.

Other examples of suitable additional polymers of this type are commercially available from sources such as Sigma-Aldrich, and include, but are not limited to, polybutadiene, poly(butadiene-co-acrylonitrile), polybutadiene-block-polyisoprene, polybutadiene-graft-poly(methyl acrylate-co-acrylonitrile), polyisoprene, and partially hydrogenated polyisoprene.

Other examples of additional polymers include aromatic group-containing copolymers, including random copolymers, block copolymers and graft copolymers. In various embodiments, the aromatic group is incorporated into the copolymer via the polymerization of styrene, and in some embodiments, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene (e.g., isobutylene). Useful block copolymers include copolymer containing (a) blocks of polystyrene, (b) blocks of a polyolefin selected from polybutadiene, polyisoprene and/or polybutene (e.g., isobutylene), and (c) optionally a third monomer (e.g., ethylene) copolymerized in the polyolefin block.

The aromatic group-containing copolymers may contain about 10% to about 50% (wt) of polymerized aromatic monomer and the molecular weight of the copolymer may be from about 50 kilodaltons to about 500 kilodaltons. In some embodiments, the molecular weight of the copolymer may be from about 300 kilodaltons to about 500 kilodaltons. In other embodiments, the molecular weight of the copolymer may be from about 100 kilodaltons to about 300 kilodaltons.

Other examples of suitable copolymers of this type are commercially available from sources such as Sigma-Aldrich and include, but are not limited to, poly(styrene-co-butadiene) (random), polystyrene-block-polybutadiene, polystyrene-block-polybutadiene-block-polystyrene, polystyrene-block-poly(ethylene-ran-butylene)-block-polystyrene, polystyrene-block-polyisoprene-block-polystyrene, polystyrene-block-polyisobutylene-block-polystyrene, poly(styrene-co-acrylonitrile), poly(styrene-co-butadiene-co-acrylonitrile) and poly(styrene-co-butadiene-co-methyl methacrylate).

Other suitable additional polymers include epichlorohydrin homopolymers and poly(epichlorohydrin-co-alkylene oxide) copolymers. In various embodiments, in the case of the copolymer, the copolymerized alkylene oxide is ethylene oxide. In some embodiments, epichlorohydrin content of the epichlorohydrin-containing polymer is from about 30% to 100% (wt), and in various embodiments, from about 50% to 100% (wt). In some embodiments, the epichlorohydrin-containing polymers have an Mw from about 100 kilodaltons to about 300 kilodaltons.

Other examples of suitable copolymers of this type are commercially available from sources such as Sigma-Aldrich and include, but are not limited to, polyepichlorohydrin and poly(epichlorohydrin-co-ethylene oxide).

One additional polymer that may be utilized in the coating composition of the present invention includes poly(ethylene-co-vinyl acetate) (pEVA). Examples of suitable polymers of this type are available commercially and include poly(ethylene-co-vinyl acetate) having vinyl acetate concentrations of from about 8% and about 90%, in various embodiments, from about 20 to about 40 weight percent and in some embodiments from about 30 to about 34 weight percent. Such polymers are generally found in the form of beads, pellets, granules, etc. It has generally been found that pEVA co-polymers with lower percent vinyl acetate become increasingly insoluble in typical solvents.

In some embodiments, coating compositions for use in this invention includes mixtures of first and second polymer components as described herein. Optionally, both first and second polymer components are purified for such use to a desired extent and/or provided in a form suitable for in vivo use. Moreover, biocompatible additives may be added, such as dyes and pigments (e.g., titanium dioxide, Solvent Red 24, iron oxide, and Ultramarine Blue); slip agents (e.g., amides such as oleyl palmitamide, N,N'-ethylene bisoleamide, erucamide, stearamide, and oleamide); antioxidants (e.g. butylated hydroxytoluene (BHT), vitamin E (tocopherol), BNX™, dilauryl thiodipropionate (DLTDP), Irganox™ series, phenolic and hindered phenolic antioxidants, organophosphites (e.g., trisnonylphenyl phosphite, Irgafos™ 168), lactones (e.g., substituted benzofuranone), hydroxylamine, and MEHQ (monomethyl ether of hydroquinone)); surfactants (e.g., anionic fatty acid surfactants (e.g., sodium lauryl sulfate, sodium dodecylbenzenesulfonate, sodium stearate, and sodium palmitate), cationic fatty acid surfactants (e.g., quaternary ammonium salts and amine salts), and nonionic ethoxylated surfactants (e.g., ethoxylated p-octylphenol)); and leachable materials (i.e., permeation enhancers) (e.g., hydrophilic polymers (e.g., poly(ethylene glycol), polyvinylpyrrolidone, and poly(vinyl alcohol)) and hydrophilic small molecules (e.g., sodium chloride, glucose)). In addition, any impurities may be removed by conventional methods available to those skilled in the art.

In some embodiments the polymer mixture includes a first polymer component comprising one or more polymers selected from the group consisting of ethylene copolymers with other alkylenes, and a second polymer component selected from the group consisting of poly (alkyl(meth)acrylates) and poly (aromatic(meth)acrylates) and having a molecular weight of optionally from about 150 kilodaltons to about 500 kilodaltons, and optionally from about 200 kilodaltons to about 400 kilodaltons.

These mixtures of polymers have proven useful with absolute polymer concentrations (i.e., the total combined concentrations of both polymers in the coating composition), of between about 0.1 and about 50 percent (by weight), and in some embodiments between about 0.1 and about 35 percent (by weight). Various polymer mixtures contain at least about 10 percent by weight of either the first polymer or the second polymer.

In some embodiments, the polymer composition may comprise about 5% to about 95% of the first and/or second polymers based on the total weights of the first and second polymers. In various embodiments, the composition may comprise about 15% to about 85% of the first and/or second polymers. In some embodiments, the composition may include about 25% to about 75% of the first and/or second polymers.

In some embodiments, the bioactive agent may comprise about 1% to about 75% of the first polymer, second polymer, and bioactive agent mixture (i.e., excluding solvents and other additives). In various embodiments, the bioactive agent may comprise about 5% to about 60% of such a mixture. In some embodiments, the bioactive agent may comprise about 25% to about 45% of such a mixture. The concentration of the bioactive agent or agents dissolved or suspended in the coating mixture can range from about 0.01 to about 90 percent, by weight, based on the weight of the final coating composition, and in various embodiments from about 0.1 to about 50 percent by weight.

The term "bioactive agent", as used herein, will refer to a wide range of biologically active materials or drugs that can be incorporated into a coating composition of the present invention. In some embodiments, the bioactive agent(s) to be incorporated do not chemically interact with the coating composition during fabrication or during the bioactive agent release process.

Bioactive agent will, in turn, refer to a peptide, protein, carbohydrate, nucleic acid, lipid, polysaccharide or combinations thereof, or synthetic or natural inorganic or organic molecule, that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include a) therapeutic nucleic acids, including antisense DNA and antisense RNA, and b) nucleic acids encoding therapeutic gene products, including plasmid DNA and viral fragments, along with associated promoters and excipients. Examples of other molecules that can be incorporated include nucleosides, nucleotides, antisense, vitamins, minerals, and steroids.

Controlled release of bioactive agent is vitally important in many medical areas, including cardiology, oncology, central nervous system disorders, neurology, immunology, diabetes control, musculoskeletal and joint diseases, ophthalmology, vaccination, respiratory, endocrinology, dermatology, and diagnostics/imaging.

Furthermore, it is recognized that thrombus formation on or around medical devices such as stents may create variations in biological agent uptake in target tissue sites and can act to either increase or decrease wall deposition according to the clot and device geometry. The embodiments of this invention further enable reliable and predictable delivery and update of bioactive agents through enhancement of the conformable, durable and stable coatings which result, regardless of flexion or other motion of the medical device substrate.

Coating compositions prepared according to this process can be used to deliver drugs such as nonsteroidal anti-inflammatory compounds, anesthetics, chemotherapeutic agents, immunotoxins, immunosuppressive agents, steroids, antibiotics, antivirals, antifungals, steroidal antiinflammatories, anticoagulants, antiproliferative agents, angiogenic agents, and anti-angiogenic agents. In various embodiments, the bioactive agent to be delivered is a hydrophobic drug having a relatively low molecular weight (i.e., a molecular weight no greater than about two kilodaltons, and optionally no greater than about 1.5 kilodaltons). For example, hydrophobic drugs such as rapamycin, paclitaxel, dexamethasone, lidocaine, triamcinolone acetonide, retinoic acid, estradiol, pimecrolimus, tacrolimus or tetracaine can be included in the coating and are released over several hours or longer.

Classes of medicaments which can be incorporated into coatings of this invention include, but are not limited to, anti-AIDS substances, anti-neoplastic substances, antibacterials, antifungals and antiviral agents, enzyme inhibitors, neurotoxins, opioids, hypnotics, antihistamines, immunomodulators (e.g., cyclosporine), tranquilizers, anti-convulsants, muscle relaxants and anti-Parkinsonism substances, antispasmodics and muscle contractants, miotics and anti-cholinergics, immunosuppressants (e.g. cyclosporine), anti-glaucoma solutes, anti-parasite and/or anti-protozoal solutes, anti-hypertensives, analgesics, anti-pyretics and anti-inflammatory agents (such as NSAIDs), local anesthetics, ophthalmics, prostaglandins, anti-depressants, anti-psychotic substances, anti-emetics, imaging agents, specific targeting agents, neurotransmitters, proteins, and cell response modifiers. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are recognized as substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, cephalosporins, and analogues thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include methyl-P-adamantane methylamine, hydroxyethoxymethylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, 1-hydroxymaleate, iodotubercidin, p-bromotetramisole, 10-($\alpha$-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl.HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacin, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(-), 3-iodotyrosine, alpha-methyltyrosine, L(-), alpha-methyltyrosine, D L(-), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (acetylsalicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which inhibit pain signals in a localized region. Examples of such anesthetics include procaine, lidocaine, tetracaine and dibucaine.

Imaging agents are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, estradiols, insulin-like growth factor, nerve growth factor, bone growth/cartilage-inducing factor (alpha and beta), and matrix metallo proteinase inhibitors. Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, DNA that encodes for the production of any of these proteins, antisense molecules, androgenic receptor blockers and statin agents.

Examples of some bioactive agents that may be used in the embodiments of the present invention include sirolimus, including analogues and derivatives thereof (including rapamycin, ABT-578, everolimus). Sirolimus has been described as a macrocyclic lactone or triene macrolide antibiotic and is produced by *Streptomyces hygroscopicus*, having a molecular formula of $C_{51}H_{79}O_{13}$ and a molecular weight of 914.2. Sirolimus has been shown to have antifungal, antitumor and immunosuppressive properties. Another suitable bioactive agent includes paclitaxel (Taxol) which is a lipophilic (i.e., hydrophobic) natural product obtained via a semi-synthetic process from *Taxus baccata* and having antitumor activity.

Other suitable bioactive agents include, but are not limited to, the following compounds, including analogues and derivatives thereof: dexamethasone, betamethasone, retinoic acid, vinblastine, vincristine, vinorelbine, etoposide, teniposide, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, melphalan, chlorambucil, ethylenimines and methylmelamines, alkyl sulfonates-busulfan, nitrosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, aminoglutethimide, estrogen, heparin, synthetic heparin salts, tissue plasminogen activator, streptokinase, urokinase, dipyridamole, ticlopidine, clopidogrel, abciximab, breveldin, cortisol, cortisone, fludrocortisone, prednisone, prednisolone, 6U-methylprednisolone, triamcinolone, triamcinolone acetonide, acetaminophen, etodalac, tolmetin, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, tacrolimus (FK-506), azathioprine, mycophenolate mofetil, vascular endothelial growth factor (VEGF), angiotensin receptor blocker, nitric oxide donors, anti-sense oligonucleotides and combinations thereof, cell cycle inhibitors, mTOR inhibitors, and growth factor signal transduction kinase inhibitors. Another suitable bioactive agent includes morpholino phosphorodiamidate oligmer.

A comprehensive listing of bioactive agents can be found in *The Merck Index*, Thirteenth Edition, Merck & Co. (2001), the entire contents of which is incorporated by reference herein. Bioactive agents are commercially available from Sigma Aldrich (e.g., vincristine sulfate). The concentration of the bioactive agent or agents dissolved or suspended in the coating mixture can range from about 0.01 to about 90 percent, by weight, based on the weight of the final coated composition. Additives such as inorganic salts, BSA (bovine serum albumin), and inert organic compounds can be used to alter the profile of bioactive agent release, as known to those skilled in the art.

In some embodiments, to provide a coating of the present invention, a coating composition is prepared to include one or more solvents, a combination of complementary polymers dissolved in the solvent, and the bioactive agent or agents dispersed in the polymer/solvent mixture. The solvent may be one in which the polymers form a true solution. The pharmaceutical agent itself may either be soluble in the solvent or form a dispersion throughout the solvent. Suitable solvents include, but are not limited to, alcohols (e.g., methanol, butanol, propanol and isopropanol), alkanes (e.g., halogenated or unhalogenated alkanes such as hexane, cyclohexane, methylene chloride and chloroform), amides (e.g., dimethylformamide), ethers (e.g., tetrahydrofuran (THF), dioxolane and dioxane), ketones (e.g., methyl ethyl ketone), aromatic compounds (e.g., toluene and xylene), nitriles (e.g., acetonitrile) and esters (e.g., ethyl acetate). In various embodiments, THF and chloroform have been found to be effective solvents due to their excellent solvency for a variety of polymers and bioactive agents of the present invention.

A coating composition of this invention can be used to coat the surface of a variety of devices, and is particularly useful for those devices that will come in contact with aqueous systems. Such devices are coated with a coating composition adapted to release bioactive agent in a prolonged and controlled manner, generally beginning with the initial contact between the device surface and its aqueous environment.

The coated composition provides a means to deliver bioactive agents from a variety of biomaterial surfaces. Various biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls, such as those polymerized from ethylene, propylene, styrene, vinyl chloride, vinyl acetate, vinyl pyrrolidone, and vinylidene difluoride. Examples of condensation polymers include, but are not limited to, nylons such as polycaprolactam, poly(lauryl lactam), poly(hexamethylene adipamide), and poly(hexamethylene dodecanediamide), and also polyurethanes, polycarbonates, polyamides, polysulfones, poly(ethylene terephthalate), poly(lactic acid), poly(glycolic acid), poly(lactic acid-co-glycolic acid), polydimethylsiloxanes, polyetheretherketone, poly(butylene terephthalate), poly(butylene terephthalate-co-polyethylene glycol terephthalate), esters with phosphorus containing linkages, non-peptide polyamino acid polymers, polyiminocarbonates, amino acid-derived polycarbonates and polyarylates, and copolymers of polyethylene oxides with amino acids or peptide sequences.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, stainless steel, and cobalt chromium. A second class of metals include the noble metals such as gold, silver, copper, and platinum. Alloys of metals may be suitable for biomaterials as well, such as nitinol (e.g. MP35). The ceramics include, but are not limited to, silicon nitride, silicon carbide, zirconia, and alumina, as well as glass, silica, and sapphire. Yet other suitable biomaterials include combinations of ceramics and metals, as well as biomaterials that are fibrous or porous in nature.

Optionally, the surface of some biomaterials can be pretreated (e.g., with a silane and/or Parylene™ coating composition in one or more layers) in order to alter the surface properties of the biomaterial. For example, in various embodiments of the present invention a layer of silane may be applied to the surface of the biomaterial followed by a layer of Parlene™. Parylene™ C is the polymeric form of the low-molecular-weight dimer of para-chloro-xylylene. Silane and/or Parylene™ C (a material supplied by Specialty Coating Systems (Indianapolis)) can be deposited as a continuous coating on a variety of medical device parts to provide an evenly distributed, transparent layer. In one embodiment, the deposition of Parylene™ is accomplished by a process termed vapor deposition polymerization, in which dimeric Parylene™ C is vaporized under vacuum at 150° C., pyrolyzed at 680° C. to form a reactive monomer, then pumped into a chamber containing the component to be coated at 25° C. At the low chamber temperature, the monomeric xylylene is deposited on the part, where it immediately polymerizes via a free-radical process. The polymer coating reaches molecular weights of approximately 500 kilodaltons.

Deposition of the xylylene monomer takes place in only a moderate vacuum (0.1 torr) and is not line-of-sight. That is, the monomer has the opportunity to surround all sides of the part to be coated, penetrating into crevices or tubes and coating sharp points and edges, creating what is called a "conformal" coating. With proper process control, it is possible to deposit a pinhole-free, insulating coating that will provide very low moisture permeability and high part protection to corrosive biological fluids.

Adherence is a function of the chemical nature of the surface to be coated. It has been reported, for instance, that tantalum and silicon surfaces can be overcoated with silicon dioxide, then with plasma-polymerized methane, and finally with Parylene™ C to achieve satisfactory adherence.

Most applications of Parylene™ C coating in the medical device industry are for protecting sensitive components from corrosive body fluids or for providing lubricity to surfaces. Typical anticorrosion applications include blood pressure sensors, cardiac-assist devices, prosthetic components, bone pins, electronic circuits, ultrasonic transducers, bone-growth stimulators, and brain probes. Applications to promote lubricity include mandrels, injection needles, cannulae, and catheters.

Also, as previously described above, the surface to which the composition is applied can itself be pretreated in other manners sufficient to improve attachment of the composition to the underlying (e.g., metallic) surface. Additional examples of such pretreatments include photografted polymers, epoxy primers, polycarboxylate resins, and physical roughening of the surface. It is further noted that the pretreatment compositions and/or techniques may be used in combination with each other or may be applied in separate layers to form a pretreatment coating on the surface of the medical device.

In some embodiments, a tie-in layer may be utilized to facilitate one or more physical and/or covalent bonds between layers. For example, the pretreatment layer may include a multi-interface system to facilitate adhesion and cohesion interaction relative to the different materials positioned at the interface of each layer. For example, the application of Parylene pretreatments to metal surfaces may be aided by a first application of a reactive organosilane reagent. A reactive organosilane reagent containing an unsaturated pendant group is capable of participating with the Parylene radicals as they deposit on the surface from the vapor phase. After cleaning of the metal surface, an organosilane reagent with an unsaturated pendant group may be applied to the metal oxide surface on a metal substrate. Without intending to be bound by theory, it appears that the silicon in the organosilane reagent couples covalently to the metal oxide, linking the organosilane group to the surface. The substrate may then be placed in a Parylene reactor and exposed to the vapor-phase Parylene process. During this process, the unsaturated pendant groups on the organosilane-treated surface can react with the Parylene diradicals depositing from the vapor phase. This forms a covalent link between the Parylene and the organosilane layer. The Parylene also forms covalent bonds to itself as it deposits. Thus, this process yields a layered surface in which the layers are covalently bonded to each other. This forms a very strong bond between the Parylene and the metal surface, resulting in high durability to mechanical challenges. Further, in some embodiments, the Parylene may physically bond with the bioactive agent delivery coating or may include a reactive acrylate group that can be reacted with the bioactive agent delivery coating to improve durability to mechanical challenges.

The coating composition of the present invention can be used in combination with a variety of devices, including those used on a temporary, transient, or permanent basis upon and/or within the body.

Compositions of this invention can be used to coat the surface of a variety of implantable devices, for example: drug-delivering vascular stents (e.g., self-expanding stents typically made from nitinol, balloon-expanded stents typically prepared from stainless steel); other vascular devices (e.g., grafts, catheters, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder and renal devices, and catheters); colostomy bag attachment devices; ophthalmic devices (e.g. ocular coils); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts).

Examples of useful devices include urinary catheters (e.g., surface-coated with antimicrobial agents such as vancomycin or norfloxacin), intravenous catheters (e.g., treated with antithrombotic agents (e.g., heparin, hirudin, coumadin), small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, benign prostate and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Examples of other suitable devices include, but are not limited to, vena cava filters, urinary dialators, endoscopic surgical tissue extractors, atherectomy catheters, clot extraction catheters, percutaneous transluminal angioplasty catheters, PTCA catheters, stylets (vascular and non-vascular), coronary guidewires, drug infusion catheters, esophageal stents, circulatory support systems, angiographic catheters, transition sheaths and dilators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Examples of medical devices suitable for the present invention include, but are not limited to catheters, implantable vascular access ports, blood storage bags, vascular stents, blood tubing, arterial catheters, vascular grafts, intraortic balloon pumps, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices").

The compositions are particularly useful for those devices that will come in contact with aqueous systems, such as bodily fluids. Such devices are coated with a coating composition adapted to release bioactive agent in a prolonged and controlled manner, generally beginning with the initial contact between the device surface and its aqueous environment. It is important to note that the local delivery of combinations of bioactive agents may be utilized to treat a wide variety of conditions utilizing any number of medical devices, or to enhance the function and/or life of the device. Essentially, any type of medical device may be coated in some fashion with one or more bioactive agents that enhances treatment over use of the individual use of the device or bioactive agent.

In various embodiments, the coating composition can also be used to coat stents, e.g., either self-expanding stents, which are typically prepared from nitinol, or balloon-expandable stents, which are typically prepared from stainless steel. Other stent materials, such as cobalt chromium alloys, can be coated by the coating composition as well.

Devices which are particularly suitable include vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of suitable balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor.

In other embodiments, the coating composition can also be used to coat ophthalmic devices, e.g. ocular coils. A therapeutic agent delivery device that is particularly suitable for delivery of a therapeutic agent to limited access regions, such as the vitreous chamber of the eye and inner ear is described in U.S. Pat. No. 6,719,750 and U.S. Patent Application Publication No. 2005/0019371 A1.

The resultant coating composition can be applied to the device in any suitable fashion (e.g., the coating composition can be applied directly to the surface of the medical device, or alternatively, to the surface of a surface-modified medical device, by dipping, spraying, ultrasonic deposition, or using any other conventional technique). The suitability of the coating composition for use on a particular material, and in turn, the suitability of the coated composition can be evaluated by those skilled in the art, given the present description. In one such embodiment, for instance, the coating comprises at least two layers which are themselves different. For instance, a base layer may be applied having bioactive agent(s) alone, or together with or without one or more of the polymer components, after which one or more topcoat layers are coated, each with either first and/or second polymers as described herein, and with or without bioactive agent. These different layers, in turn, can cooperate in the resultant composite coating to provide an overall release profile having certain desired characteristics, and in some embodiments is for use with bioactive agents of high molecular weight. In various embodiments, the composition is coated onto the device surface in one or more applications of a single composition that includes first and second polymers, together with bioactive agent. However, as previously suggested a pretreatment layer or layers may be first applied to the surface of the device, wherein subsequent coating with the composition may be performed onto the pretreatment layer(s). The method of applying the coating composition to the device is typically governed by the geometry of the device and other process considerations. The coating is subsequently cured by evaporation of the solvent. The curing process can be performed at room or elevated temperature, and optionally with the assistance of vacuum and/or controlled humidity.

It is also noted that one or more additional layers may be applied to the coating layer(s) that include bioactive agent. Such layer(s) or topcoats can be utilized to provide a number of benefits, such as biocompatibility enhancement, delamination protection, durability enhancement, bioactive agent release control, to just mention a few. In one embodiment the topcoat may include one or more of the first, second, and/or additional polymers described herein without the inclusion of a bioactive agent. In some embodiments, the topcoat includes a second polymer that is a poly(alkyl(meth)acrylate). An example of one embodiment of a poly(alkyl(meth)acrylate) includes poly (n-butyl methacrylate). In another embodiment, the first or second polymers could further include functional groups (e.g. hydroxy, thiol, methylol, amino, and amine-reactive functional groups such as isocyanates, thioisocyanates, carboxylic acids, acyl halides, epoxides, aldehydes, alkyl halides, and sulfonate esters such as mesylate, tosylate, and tresylate) that could be utilized to bind the topcoat to the adjacent coating composition. In another embodiment of the present invention one or more of the pretreatment materials (e.g. Parylene™) may be applied as a topcoat. Additionally, biocompatible topcoats (e.g. heparin, collagen, extracellular matrices, cell receptors . . . ) may be applied to the coating composition of the present invention. Such biocompatible topcoats may be adjoined to the coating composition of the present invention by utilizing photochemical or thermochemical techniques known in the art. Additionally, release layers may be applied to the coating composition of the present invention as a friction barrier layer or a layer to protect against delamination. Examples of biocompatible topcoats that may be used include those disclosed in U.S. Patent Nos. 4,979,959 and 5,744,515.

The polymer composition for use in this invention is generally biocompatible, e.g., such that it results in no significant induction of inflammation or irritation when implanted. In addition, the polymer combination is generally useful throughout a broad spectrum of both absolute concentrations and relative concentrations of the polymers. This means that the physical characteristics of the coating, such as tenacity, durability, flexibility and expandability, will typically be adequate over a broad range of polymer concentrations. In turn, the ability of the coating to control the release rates of a variety of bioactive agents may be manipulated by varying the absolute and relative concentrations of the polymers.

Additionally, the coatings of the present invention are generally hydrophobic and limit the intake of aqueous fluids. For example, many embodiments of the present invention are coating compositions including two or more hydrophobic polymers wherein the resulting coating shows <10% (wt) weight change when exposed to water, and in some embodiments <5% (wt) weight change when exposed to water.

A coating composition can be provided in any suitable form, e.g., in the form of a true solution, or fluid or paste-like emulsion, mixture, dispersion or blend. In various embodiments, polymer combinations of this invention are capable of being provided in the form of a true solution, and in turn, can be used to provide a coating that is both optically clear (upon microscopic examination), while also containing a significant amount of bioactive agent. In turn, the coated composition will generally result from the removal of solvents or other volatile components and/or other physical-chemical actions (e.g., heating or illuminating) affecting the coated composition in situ upon the surface.

A further example of a coating composition embodiment may include a configuration of one or more bioactive agents within an inner matrix structure, for example, bioactive agents within or delivered from a degradable encapsulating matrix or a microparticle structure formed of semipermeable cells and/or degradable polymers. One or more inner matrices may be placed in one or more locations within the coating composition and at one or more locations in relation to the substrate. Examples of inner matrices, for example degradable encapsulating matrices formed of semipermeable cells and/or degradable polymers, are disclosed and/or suggested in U.S. Publication No. 20030129130, U.S. Patent Application Ser. No. 60/570,334 filed May 12, 2004, U.S. Patent Application Ser. No. 60/603,707, filed Aug. 23, 2004, U.S. Publication No. 20040203075, filed Apr. 10, 2003, U.S. Publication No. 20040202774 filed on Apr. 10, 2003, and U.S. patent application Ser. No. 10/723,505, filed Nov. 26, 2003, the entire contents of which are incorporated by reference herein.

The overall weight of the coating upon the surface may vary depending on the application. However, in some embodiments, the weight of the coating attributable to the bioactive agent is in the range of about one microgram to about 10 milligram (mg) of bioactive agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In various embodiments, the weight of the coating attributable to the bioactive agent is between about 0.005 mg and about 10 mg, and in some embodiments, between about 0.01 mg and about 1 mg of bioactive agent per $cm^2$ of the gross surface area of the device. This quantity of bioactive agent is generally required to provide desired activity under physiological conditions.

In turn, in various embodiments, the final coating thickness of a coated composition will typically be in the range of about 0.1 micrometers to about 100 micrometers, and in some embodiments between about 0.5 micrometers and about 25 micrometers. This level of coating thickness is generally required to provide an adequate concentration of drug to provide adequate activity under physiological conditions.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by the embodiments described by the language of the claims and the equivalents of those embodiments. Unless otherwise indicated, all percentages are by weight.

EXAMPLES

Test Procedures

The potential suitability of particular coated compositions for in vivo use can be determined by a variety of screening methods, examples of each of which are described herein. Not all of these test procedures were used in connection with the example included in this application, but they are described here to enable consistent comparison of coatings in accordance with the invention.

Sample Preparation Procedure

Stainless steel stents used in the following examples were manufactured by Laserage Technology Corporation, Waukegan, Ill. In some cases, the metal surface of the stents may be coated without any pretreatment beyond washing. In other cases, a primer may be applied to the stents by first cleaning the stents with aqueous base, then pre-treating with a silane followed by vapor deposition of Parylene™ polymer. The silane used may be [3-(methacroyloxy)propyl] trimethoxysilane, available from Sigma-Aldrich Fine Chemicals as Product No. 44,015-9. The silane may be applied as essentially a monolayer by mixing the silane at a low concentration in 50/50 (vol) isopropanol/water, soaking the stents in the aqueous silane solution for a suitable length of time to allow the water to hydrolyze the silane and produce some cross-linking, washing off residual silane, then baking the silane-treated stent at 100° C. for conventional periods of time. Following the silane treatment, Parylene™ C coating (available from Union Carbide Corporation, Danbury, Conn.) may be vapor-deposited at a thickness of about 1 mm. Prior to coating, the stents should be weighed on a microbalance to determine a tare weight.

Bioactive agent/polymer solutions may be prepared at a range of concentrations in an appropriate solvent (typically tetrahydrofuran or chloroform), in the manner described herein. In all cases the coating solutions are applied to respective stents by spraying, and the solvent is allowed to evaporate under ambient conditions. The coated stents are then re-weighed to determine the mass of coating and consequently the mass of polymer and bioactive agent.

Rapamycin Release Assay Procedure

The Rapamycin Release Assay Procedure, as described herein, was used to determine the extent and rate of release of an exemplary bioactive agent, rapamycin, under in vitro elution conditions. Spray-coated stents prepared using the Sample Preparation Procedure were placed in sample baskets into 10 milliliters of Sotax™ dissolution system (elution media containing 2% (wt) surfactant/water solution, available from Sotax Corporation, Horsham, Pa.). Amount of bioactive agent elution was monitored by UV spectrometry over the course of several days. The elution media was held at 37° C. After the elution measurements, the stents were removed, rinsed, dried, and weighed to compare measured bioactive agent elution to weighed mass loss.

Dexamethasone Release Assay Procedure

The Dexamethasone Release Assay Procedure, as described herein, may be used to determine the extent and rate of dexamethasone release under in vitro conditions. Spray-coated stents made using the Sample Preparation Procedure are placed in 10 milliliters of pH 7 phosphate buffer solution ("PBS") contained in an amber vial. A magnetic stirrer bar is added to the vial, and the vial with its contents are placed into a 37° C. water bath. After a sample interval, the stent is removed and placed into a new buffer solution contained in a new vial. Dexamethasone concentration in the buffer is measured using ultraviolet spectroscopy and the concentration converted to mass of bioactive agent released from the coating. After the experiment, the stent is dried and weighed to correlate actual mass loss to the loss measured by the elution experiment.

Durability Test Procedure

The durability of the coated composition can be determined by the following manner. To simulate use of the coated devices, the coated stents are placed over sample angioplasty balloons. The stent is then crimped onto the balloon using a laboratory test crimper (available from Machine Solutions, Brooklyn, N.Y.). The stent and balloon are then placed in a phosphate buffer bath having a pH of 7.4 and temperature of 37° C. After 5 minutes of soaking, the balloon is expanded using air at 5 atmospheres (3800 torr) of pressure. The balloon is then deflated, and the stent is removed.

The stent is then examined by optical and scanning electron microscopy to determine the amount of coating damage caused by cracking and/or delamination and a rating may be assigned. Coatings with extensive damage are considered unacceptable for a commercial medical device. The "Rating" is a qualitatitive scale used to describe the amount of damage to the coating from the stent crimping and expansion procedure based on optical microscopy examination by an experienced coating engineer. A low rating indicates a large percentage of the coating cracked, smeared, and/or delaminated from the surface. For example, a coating with a rating of ten shows no damage while one with a rating of 1 will show a majority of the coating damaged to the point where clinical efficacy may be diminished. Commercially attractive coatings typically have a rating of nine or higher.

Stress-Strain Measurement Test Procedure

Polymer films can be prepared by hot pressing polymer beads at 100° C. in a constant film maker kit to a thickness of approximately 0.5 mm. The resulting films are cut into strips using a razor blade. A Q800 Dynamic Mechanical Analyzer (available from Texas Instruments, Dallas, Tex.) may be fitted with a film tension clamp. Each sample is equilibrated at 35° C. for five minutes prior to straining the sample. Then the sample is loaded into the clamp such that the sample length is between 5 and 7 mm in length. A static force of 0.01N is applied to each sample throughout the measurements. Simultaneously, a 0.5 N/min force is applied to the sample until the movable clamp reaches its maximum position. Films are elongated at constant stress and the average tensile modulus (i.e., the initial slope of the stress-strain curve, in MPa) can be determined.

Example 1

Release of Rapamycin from Poly(ethylene-co-propylene) and Poly(butyl methacrylate)

Three solutions were prepared for coating the stents. The solutions included mixtures of poly(ethylene-co-propylene) ("PEPP", available from Sigma-Aldrich Fine Chemicals, Milwaukee, Wis., as Product No. 18,962-6, contains 60% (mole) ethylene, having Mw of approximately 170 kilodaltons), "PBMA" and "RAPA" ("PBMA", available from Sigma-Aldrich Fine Chemicals as Product No. 18,152-8, having a weight average molecular weight (Mw) of about 337 kilodaltons), and rapamycin ("RAPA", available from LC Laboratories, Woburn, Mass.) dissolved in THF to form a homogeneous solution. The stents were not given a primer pre-treatment.

The solutions were prepared to include the following ingredients at the stated weights per milliliter of THF:

1) 16 mg/ml PEPP/4 mg/ml PBMA/10 mg/ml RAPA
2) 10 mg/ml PEPP/10 mg/ml PBMA/10 mg/ml RAPA
3) 4 mg/ml PEPP/16 mg/ml PBMA/10 mg/ml RAPA

Using the Sample Preparation Procedure, two stents were spray coated using each solution. After solvent removal via ambient evaporation, the drug elution for each coated stent was monitored using the Rapamycin Release Assay Procedure.

Figure 1:
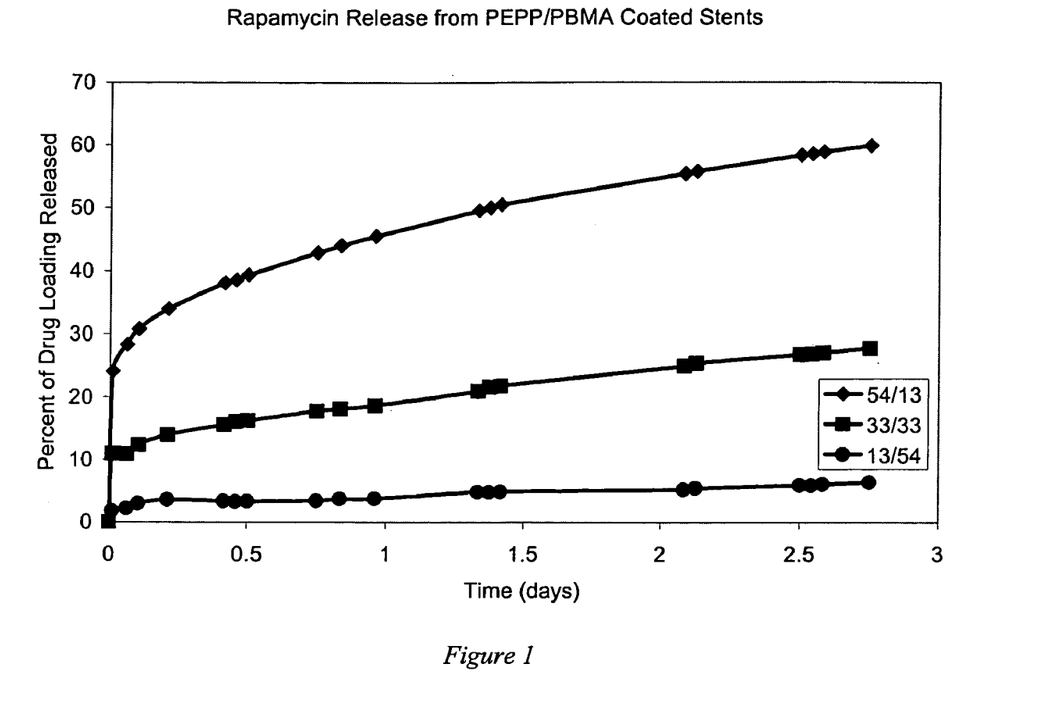

Results, provided in FIG. 1, demonstrate the ability to control the elution rate of rapamycin, a pharmaceutical agent, from a coated stent surface by varying the relative concentrations of PEPP and PBMA in the polymer mixture as described herein.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A composition for coating the surface of a medical device with at least one bioactive agent in a manner that permits the coated surface to release the bioactive agent over time when implanted in vivo, the composition comprising at least one bioactive agent in combination with a plurality of polymers, including a first polymer component comprising at least one ethylene copolymer with other alkylenes and a second polymer component comprising a polymer selected from the group consisting of poly(alkyl(meth)acrylates) and poly(aromatic(meth)acrylates).

2. A composition according to claim 1 wherein the first polymer component is selected from the group consisting of poly(ethylene-co-propylene), poly(ethylene-co-1-butene), poly(ethylene-co-1-butene-co-1-hexene), poly(ethylene-co-1-octene) and poly(ethylene-co-propylene-co-5-methylene-2-norborene).

3. A composition according to claim 1 wherein the first polymer component includes straight chain alkylenes.

4. A composition according to claim 1 wherein the first polymer component includes branched alkylenes.

5. A composition according to claim 1 wherein the first polymer component includes substituted alkylenes.

6. A composition according to claim 1 wherein the first polymer component includes copolymers prepared from alkylenes that comprise from 3 to 8 carbon atoms.

7. A composition according to claim 6 wherein the first polymer component includes copolymers prepared from alkylenes that comprise from 3 to 4 carbon atoms.

8. A composition according to claim 1, the first polymer component having a molecular weight from about 30 kilodaltons to about 500 kilodaltons.

9. A composition according to claim 1 wherein the composition includes at least one additional polymer selected from the group consisting of poly(alkylene-co-alkyl(meth) acrylates), polybutenes, diolefin-derived non-aromatic polymers or copolymers, aromatic group-containing copolymers, epichlorohydrin-containing polymers and poly (ethylene-co-vinyl acetate).

10. A composition according to claim 9 wherein the poly (alkylene-co-alkyl(meth)acrylates) are selected from the group consisting of poly(ethylene-co-methyl acrylate), poly (ethylene-co-ethyl acrylate), poly(ethylene-co-2-ethylhexyl acrylate) and poly(ethylene-co-butyl acrylate), the polybutenes are selected from the group consisting of polyisobutylene, poly-1-butene and poly-2-butene, the diolefin-derived non-aromatic polymer or copolymer is selected from the group consisting of polybutadienes prepared by the polymerization of cis-, trans- and/or 1,2-monomer units, and polyisoprenes prepared by the polymerization of cis-1,4- and/or trans-1,4-monomer units, the aromatic group-containing copolymers include a copolymer derived from copolymerization of styrene monomer and one or more monomers selected from the group consisting of butadiene, isoprene, acrylonitrile, a $C_1$-$C_4$ alkyl (meth)acrylate and butene, the epichlorohydrin-containing polymers are selected from the group consisting of epichlorohydrin homopolymers and poly (epichlorohydrin-co-alkylene oxide) copolymers and the poly (ethylene-co-vinyl acetate) polymers have a vinyl acetate concentration from about 8% to about 90%.

11. A composition according to claim 1 wherein the poly (alkyl(meth)acrylate) includes an alkyl chain length from two to eight carbons.

12. A composition according to claim 1, the poly(alkyl (meth)acrylate) having a molecular weight from about 50 kilodaltons to about 900 kilodaltons.

13. A composition according to claim 1 wherein the poly (alkyl(meth)acrylate) is selected from the group consisting of poly(n-butyl methacrylate), poly(n-butyl methacrylate-co-isobutyl methacrylate), and poly(t-butyl methacrylate).

14. A composition according to claim 1 wherein the poly (aromatic(meth)acrylate) includes aryl groups having from six to sixteen carbon atoms.

15. A composition according to claim 1, the poly(aromatic (meth)acrylate) having a molecular weight from about 50 kilodaltons to about 900 kilodaltons.

16. A composition according to claim 1 wherein the poly (aromatic(meth)acrylate) is selected from the group consisting of poly(aryl (meth)acrylates), poly(aralkyl (meth)acrylates), poly(alkaryl (meth)acrylates), poly(aryloxyalkyl (meth)acrylates), and poly (alkoxyaryl (meth)acrylates).

17. A composition according to claim 16, wherein the poly(aryl (meth)acrylates) are selected from the group consisting of poly(9-anthracenyl methacrylate), poly(chlorophenyl acrylate), poly(methacryloxy-2-hydroxybenzophenone), poly(methacryloxybenzotriazole), poly(naphthyl acrylate), poly(naphthylmethacrylate), poly-4-nitrophenylacrylate, poly(pentachloro(bromo, fluoro) acrylate) and methacrylate, poly(phenyl acrylate) and poly(phenyl methacrylate); the poly(aralkyl (meth)acrylates) are selected from the group consisting of poly(benzyl acrylate), poly(benzyl methacrylate), poly(2-phenethyl acrylate), poly(2-phenethyl methacrylate) and poly(1-pyrenylmethyl methacrylate); the poly (alkaryl(meth)acrylates) are selected from the group consisting of poly(4-sec-butylphenyl methacrylate), poly(3-ethylphenyl acrylate), and poly(2-methyl-1-naphthyl methacrylate); the poly(aryloxyalkyl (meth)acrylates) are selected from the group consisting of poly(phenoxyethyl acrylate), poly(phenoxyethyl methacrylate), and poly(polyethylene glycol phenyl ether acrylate) and poly(polyethylene glycol phenyl ether methacrylate) with varying polyethylene glycol molecular weights; and the poly(alkoxyaryl(meth)acrylates) are selected from the group consisting of poly(4-methoxyphenyl methacrylate), poly(2-ethoxyphenyl acrylate) and poly(2-methoxynaphthyl acrylate).

18. A composition according to claim 1 wherein the composition further comprises a solvent in which the first and second polymer components form a true solution.

19. A composition according to claim 1 wherein the bioactive agent is dissolved or suspended in the coating mixture at a concentration of 0.01% to 90% by weight.

20. A composition according to claim 1 wherein the device is one that undergoes flexion and expansion in the course of implantation or use in vivo.

21. A composition according to claim 1 wherein the composition permits the amount and rate of release of agent(s) from the medical device to be controlled by adjusting the relative types and concentrations of the first and second polymer components in the mixture.

22. A combination comprising a medical device and a composition for coating the surface of the medical device with at least one bioactive agent in a manner that permits the coated surface to release the bioactive agent over time when implanted in vivo, the composition comprising at least one bioactive agent in combination with a plurality of polymers, including a first polymer component comprising at least one ethylene copolymer with other alkylenes and a second polymer component comprising a polymer selected from the group consisting of poly(alkyl(meth)acrylates) and poly(aromatic(meth)acrylates).

23. The combination of claim 22 wherein a pretreatment coating, adapted to alter the surface properties of the medical device, is applied to the surface of the medical device.

24. The combination of claim 22 wherein the first polymer component is selected from the group consisting of poly(ethylene-co-propylene), poly(ethylene-co-1-butene), poly(ethylene-co-1-butene-co-1-hexene), poly(ethylene-co-1-octene) and poly(ethylene-co-propylene-co-5-methylene-2-norborene).

25. The combination of claim 22 wherein the first polymer component includes straight chain alkylenes.

26. The combination of claim 22 wherein the first polymer component includes branched alkylenes.

27. The combination of claim 22 wherein the first polymer component includes substituted alkylenes.

28. The combination of claim 22 wherein the composition includes at least one additional polymer selected from the group consisting of poly(alkylene-co-alkyl(meth)acrylates), polybutenes, diolefin-derived non-aromatic polymers or copolymers, aromatic group-containing copolymers, epichlorohydrin-containing polymers and poly(ethylene-co-vinyl acetate).

29. The combination of claim 23 wherein the pretreatment composition is selected from the group consisting of Parylene™, silane, photografted polymers, epoxy primers, polycarboxylate resins and combinations thereof.

30. The combination of claim 22 wherein the composition permits the amount and rate of release of agent(s) from the medical device to be controlled by adjusting the relative types and concentrations of the first and second polymer components in the mixture.

31. A composition for coating the surface of a medical device with at least one bioactive agent in a manner that permits the coated surface to release the bioactive agent over time when implanted in vivo, the composition comprising at least one bioactive agent in combination with a plurality of polymers, including a first polymer component comprising at least one ethylene copolymer with other alkylenes and a second polymer component comprising a polymer selected from the group consisting of poly(alkyl(meth)acrylates) and poly(aromatic(meth)acrylates), wherein the composition includes at least one additional polymer selected from the group consisting of poly(alkylene-co-alkyl(meth)acrylates), polybutenes, diolefin-derived non-aromatic polymers or copolymers, aromatic group-containing copolymers, epichlorohydrin-containing polymers and poly(ethylene-co-vinyl acetate).

32. A composition according to claim 31 wherein the first polymer component is selected from the group consisting of poly(ethylene-co-propylene), poly(ethylene-co-1-butene), poly(ethylene-co-1-butene-co-1-hexene), poly(ethylene-co-1-octene) and poly(ethylene-co-propylene-co-5-methylene-2-norborene).

33. A method of coating the surface of a medical device, the method comprising the steps of providing a composition including at least one bioactive agent in combination with a plurality of polymers, including a first polymer component comprising at least one ethylene copolymer with other alkylenes and a second polymer component comprising a polymer selected from the group consisting of poly(alkyl(meth)acrylates) and poly(aromatic(meth)acrylates), and applying the composition to the surface of the device.

34. A combination comprising a stent and a composition for coating the surface of a stent with at least one bioactive agent in a manner that permits the coated surface to release the bioactive agent over time when implanted in vivo, the composition comprising at least one bioactive agent in combination with a plurality of polymers, including a first polymer component comprising a poly(ethylene-co-propylene), a second polymer component comprising poly(n-butyl methacrylate), a solvent in which the first and second polymer components form a true solution, and at least one biocompatible additive, and further comprising a pretreatment layer including a multi-interface system to facilitate adhesion and cohesion interaction relative to the stent and coating composition.

35. A combination according to claim 34, wherein the bioactive agent is selected from the group consisting of rapamycin, paclitaxel, dexamethasone, and estradiol.

36. A combination according to claim 34, wherein the stent includes a material selected from the group consisting of polymers, tissue, metals, ceramics, and combinations thereof.

37. A combination according to claim 36, wherein the polymers include polycarbonates and the metals are selected from the group consisting of titanium, stainless steel, gold, silver, and nitinol.

38. A combination according to claim 34, wherein the solvent is selected from the group consisting of tetrahydrofuran, chloroform, methylene chloride, toluene, cyclohexane and combinations thereof.

39. A combination according to claim 34, wherein the biocompatible additive includes one or more antioxidants selected from the group consisting of butylated hydroxytoluene, vitamin E, BNX, and dilauryl thiodipropionate.

40. A combination according to claim 34, wherein the pretreatment layer includes organosilane and Parylene™.

41. A composition according to claim 1, further comprising a pretreatment layer including a multi-interface system to facilitate adhesion and cohesion interaction relative to the medical device and composition.

42. A composition according to claim 41, wherein the pretreatment layer includes organosilane and Parylene™.

43. A combination comprising a medical device and a composition for coating the surface of a medical device with at least one bioactive agent in a manner that permits the coated surface to release the bioactive agent over time when implanted in vivo, the composition comprising at least one bioactive agent in combination with a plurality of polymers, including a first polymer component comprising a poly(ethylene-co-propylene), a second polymer component comprising poly(n-butyl methacrylate), a solvent in which the first and second polymer components form a true solution selected from the group consisting of tetrahydrofuran, chloroform, methylene chloride, and cyclohexane, and at least one biocompatible additive including one or more antioxidants selected from the group consisting of butylated hydroxytoluene, vitamin E, BNX, and dilauryl thiodipropionate, and further comprising a pretreatment layer including a multi-interface system to facilitate adhesion and cohesion interaction relative to the medical device and coating composition.

44. A combination according to claim 43, wherein the bioactive agent is selected from the group consisting of rapamycin, paclitaxel, dexamethasone, and estradiol.

45. The combination of claim 43 further comprising a topcoat including poly(butyl methacrylate).

46. The combination of claim 43, wherein the medical device comprises a stent.

* * * * *